US010112887B2

(12) United States Patent
Goussev et al.

(10) Patent No.: US 10,112,887 B2
(45) Date of Patent: Oct. 30, 2018

(54) CATALYSTS BASED ON AMINO-SULFIDE LIGANDS FOR HYDROGENATION AND DEHYDROGENATION PROCESSES

(71) Applicants: Dmitri Goussev, Waterloo (CA); Denis Spasyuk, Calgary (CA); Samantha Smith, Waterloo (CA)

(72) Inventors: Dmitri Goussev, Waterloo (CA); Denis Spasyuk, Calgary (CA); Samantha Smith, Waterloo (CA)

(*) Notice: Subject to any disclaimer, the term of this patent is extended or adjusted under 35 U.S.C. 154(b) by 0 days.

(21) Appl. No.: 15/286,975

(22) Filed: Oct. 6, 2016

(65) Prior Publication Data
US 2017/0073298 A1 Mar. 16, 2017

Related U.S. Application Data

(63) Continuation of application No. 14/426,049, filed as application No. PCT/CA2013/050679 on Sep. 4, 2013, now abandoned.
(Continued)

(51) Int. Cl.
| | |
|---|---|
| *C07C 67/40* | (2006.01) |
| *C07C 323/25* | (2006.01) |
| *C07C 5/03* | (2006.01) |
| *C07C 209/52* | (2006.01) |
| *C01B 3/26* | (2006.01) |
| *C07C 5/08* | (2006.01) |
| *C07C 45/00* | (2006.01) |
| *C07C 29/147* | (2006.01) |
| *C07C 41/18* | (2006.01) |
| *C07C 67/00* | (2006.01) |
| *B01J 31/18* | (2006.01) |
| *B01J 31/22* | (2006.01) |
| *B01J 31/20* | (2006.01) |
| *B01J 31/24* | (2006.01) |

(Continued)

(52) U.S. Cl.
CPC ........... *C07C 67/40* (2013.01); *B01J 31/1805* (2013.01); *B01J 31/1895* (2013.01); *B01J 31/20* (2013.01); *B01J 31/22* (2013.01); *B01J 31/226* (2013.01); *B01J 31/2295* (2013.01); *B01J 31/2404* (2013.01); *C01B 3/02* (2013.01); *C01B 3/04* (2013.01); *C01B 3/26* (2013.01); *C07C 5/03* (2013.01); *C07C 5/08* (2013.01); *C07C 29/147* (2013.01); *C07C 41/18* (2013.01); *C07C 45/002* (2013.01); *C07C 67/00* (2013.01); *C07C 209/52* (2013.01); *C07C 323/25* (2013.01); *C07F 15/0026* (2013.01); *C07F 15/0046* (2013.01); *C07F 15/0053* (2013.01); *B01J 2231/641* (2013.01); *B01J 2231/643* (2013.01); *B01J 2231/645* (2013.01); *B01J 2231/70* (2013.01); *B01J 2231/763* (2013.01); *B01J 2531/0238* (2013.01); *B01J 2531/821* (2013.01); *B01J 2531/825* (2013.01); *C01B 2203/0277* (2013.01); *C01B 2203/1064* (2013.01); *C07C 2531/22* (2013.01); *C07C 2531/24* (2013.01); *Y02E 60/364* (2013.01)

(58) Field of Classification Search
CPC .... B01J 31/1805; B01J 31/1895; B01J 31/20; B01J 31/226; B01J 31/2295; B01J 31/2404; B01J 2231/641; B01J 2231/06; C01B 3/02; C01B 3/04; C01B 3/26; C01B 2203/0277; C01B 2203/1064; C01B 2531/22; C07C 209/52; C07C 29/147; C07C 23/25; C07C 41/18; C07C 45/002; C07C 5/03; C07C 5/08; C07C 67/00; C07C 67/40; C07C 2531/24; C07F 15/0026; C07F 15/0046; C07F 15/0053; Y02E 60/364

See application file for complete search history.

(56) References Cited

U.S. PATENT DOCUMENTS 7,250,526 B2 * 7/2007 Blacker ................ B01J 31/1805
502/152
2002/0173683 A1 * 11/2002 Chen .................... B01J 31/0212
585/250

FOREIGN PATENT DOCUMENTS

| WO | 2007/001649 A2 | 1/2007 |
| WO | 2009/131769 A1 | 10/2009 |
| WO | WO2009/131769 | * 10/2009 |

OTHER PUBLICATIONS

Zhang et al., "Efficient Homogeneous Catalytic Hydrogenation of Esters to Alcohols," Angew. Chem. Int. Ed., 2006, 45, 1113-1115.*
(Continued)

*Primary Examiner* — Pancham Bakshi
*Assistant Examiner* — Mark R Luderer
(74) *Attorney, Agent, or Firm* — Robert C. Netter, Jr.; Dann, Dorfman, Herrell and Skillman, P.C.

(57) ABSTRACT

The present application discloses novel amino-sulfide metal catalysts for organic chemical syntheses including hydrogenation (reduction) of unsaturated compounds or dehydrogenation of substrates. The range of hydrogenation substrate compounds includes esters, lactones, oils and fats, resulting in alcohols, diols, and triols as reaction products. The catalysts of current application can be used to catalyze a hydrogenation reaction under solvent free conditions. The present catalysts also allow the hydrogenation to proceed without added base, and it can be used in place of the conventional reduction methods employing hydrides of the main-group elements. Furthermore, the catalysts of the present application can catalyze a dehydrogenation reaction under homogenous and/or acceptorless conditions. As such, the catalysts provided herein can be useful in substantially reducing cost and improving the environmental profile of manufacturing processes for a variety of chemicals.

20 Claims, 4 Drawing Sheets

Related U.S. Application Data

(60) Provisional application No. 61/696,780, filed on Sep. 4, 2012.

(51) Int. Cl.
- *C01B 3/02* (2006.01)
- *C01B 3/04* (2006.01)
- *C07F 15/00* (2006.01)

(56) References Cited

OTHER PUBLICATIONS

Sellman et al., "Transition-metal complexes with sulfur ligands. Part 37. Iron, molybdenum, and ruthenium complexes with pentadentate OS4 and NHS4 ligands combining thiolato, thioether, and ether or amine donor functions: synthesis, structures, and reactivity of carbon monoxide, nitric oxide, trimethylphosphine and hydrazine derivatives," Inorg. Ch.*

Wolfson et al., "Glycerol as solvent and hydrogen donor in transfer hydrogenation-dehydrogenation reactions," Tetrahedron Letters, 50(2009) 5951-5953.*

Page et al., "Pyridine-2,6-bis(thioether) (SNS) Complexes of Ruthenium as Catalysts for Transfer Hydrogenation," Organometallics, 2010, 29 (17), pp. 3790-3798 (Year: 2010).*

Ahmadi, Ebrahim et al., "High Productive Ethylene Trimerizataion Catalyst Based on CrCl3/SNS Ligands", Catal. Lett., 141: 1191-1198 (2011).

Ambundo, Edna A. et al., "Influence of Coordination Geometry upon Copper (II/I) Redox Potentials. Physical Parameters for Twelve Copper Tripodal Ligand Complexes", Inorg. Chem., 38: 4233-4242 (1999).

Bai Shi-Qiang et al., "Isolation of an [SNS]Pd(ii) pincer with a water ladder and its Suzuki coupling activity in water", Chem. Commun.

Bai, Shi-Qiang et al., "Crystallographic analysis of different water-halide cluster blends in cationic [(SNS)Pd11] pincer aomplexes", Cryst. Eng. Comm., 12: 226-233 (2010).

Blomenkemper, Marc et al., "Copper(II) complexes of aliphatic tridentate amine/dithioether ligands—Synthesis and molecular structures", Inorganica Chimica Acta, 390: 143-147 (2012).

Downing, Stephen P., "Bis(alkylthioethyl)amine Complexes of Molybdenum", Organometalliles, 28: 2417-2422 (2009).

McGuinness, David S. et al., "Ethylene Trimerization with Mixed-Donor Ligand (N,P.S) Chromium Complexes: Effect of Ligand Structure on Activity and Selectivity", Organometallics, 24: 552-556 (2005).

Sellmann, Dieter et al., "Transition-Metal Complexes with Sulfur Ligands", Inorg. Chem., 27: 4183-4190 (1988).

Spasyuk, Denis et al., "Replacing Phosphorus with Sulfur for the Efficient Hydrogenation of Esters", Angew. Chem. Int. Ed., 52: 2538-2542 (2013).

Spasyuk, Denis et al., "Acceptorless Dehydrogenative Coupling of Ethanol and Hydrogenation of Esters and Imines", Organometallics, 31: 5239-5242 (2012).

Zhang, Jing et al., "Efficient Homogeneous Catalytic Hydrogenation of Esters to Alcohols", Angew. Chem. Int. Ed., 45: 1113-1115 (2006).

International Preliminary Report on Patentability, dated Dec. 22, 2014, issued in corresponding International Application No. PCT/CA2013/050679.

International Search Report issued in corresponding International Application No. PCT/CA2013/050679.

* cited by examiner

CATALYSTS BASED ON AMINO-SULFIDE LIGANDS FOR HYDROGENATION AND DEHYDROGENATION PROCESSES

CROSS-REFERENCE TO RELATED APPLICATIONS

This application is a continuation of U.S. patent application Ser. No. 14/426,049, filed Mar. 4, 2015, which is a § 371 of International Application No. PCT/CA2013/050679, filed Sep. 4, 2013, which claims the benefit of U.S. Provisional Application No. 61/696,780, filed Sep. 4, 2012. The entire disclosure of each of the aforesaid applications is incorporated by reference in the present application.

FIELD OF THE INVENTION

The present invention pertains to catalysts. More specifically, the present invention pertains to catalysts useful in hydrogenation and dehydrogenation reactions.

INTRODUCTION

Reduction of polar C═X (X═O, N) bonds is one of the most fundamental organic reactions and is useful for the synthesis of a variety of organic alcohols and amines. Reduction of esters and imines is typically accomplished using main-group hydride reagents, such as $LiAlH_4$, or using molecular hydrogen. The use of the hydride reducing reagents is inconvenient and expensive, particularly on a large scale; furthermore, this approach generates large amounts of chemical waste. The hydride reduction method can be dangerously exothermic at the stage of quenching and it can be difficult to control. The catalytic reduction of esters under hydrogen gas is, in all respects, a very attractive 'green' alternative to the classical hydride reduction.

A key component of the ester reduction with molecular hydrogen is the catalytic system utilized in the process. The catalyst system should ideally be able to rapidly bind and split molecular hydrogen to give a transition-metal hydride. The development of highly efficient and useful catalysts and catalytic systems for hydrogenation of lactones, esters, oils, and fats is an important need in chemistry. Particularly, developing hydrogenation processes operating in the temperature range of 20 to 100° C. and using less than 500 ppm (0.05 mol %) catalyst under relatively low $H_2$ pressure (1-50 bar) is highly desirable. Among the few catalysts and catalytic systems capable of converting esters and lactones into alcohols and diols under hydrogen gas, the ones that are presently most useful and efficient are complexes of ruthenium with bidentate phosphine-amine and tetradentate phosphine-imine ligands (described in Publication No. US 2010/0280273 A1, WO 2012/052996 A2, and in Angew. Chem. Int. Ed. 2007, 46, 7473). The ruthenium catalyst loadings of 500-1000 ppm (0.05-0.1 mol %) could be used in this previous system, however, the system has a few major drawbacks, including relatively poor efficiency (low turnover numbers even at 100-110° C.) and often the need for a large (5-10 mol %) amount of base, such as NaOMe, thereby reducing the product selectivity and generating large amounts of chemical waste from product neutralization and extensive purification.

The development of green chemical processes and the use of biomass for hydrogen production have attracted much attention in recent years. Furthermore, acceptorless dehydrogenative coupling of primary alcohols is an interesting transformation which leads to esters, imines, amines, or amides. Oxidant-free, catalytic dehydrogenation of alcohols is of great importance for the chemical industry. A significant advance in dehydrogenation of bio-alcohols (chiefly ethanol) has been achieved with heterogeneous catalysts, however, at the cost of using harsh reaction conditions: high temperature (>200° C.) and pressure. Therefore, designing well-defined homogeneous catalysts for alcohol dehydrogenation under mild conditions represents an important scientific and practical goal. There has been little progress in the area of acceptorless dehydrogenation of primary alcohols since Cole-Hamilton and co-workers demonstrated dehydrogenation of ethanol catalyzed by $[RuH_2(N_2)(PPh_3)_3]$, where an excess of NaOH, high temperature (150° C.), and an intense light source were needed to achieve TOF=210 $h^{-1}$, after 2 h (D. Morton, D. J. Cole-Hamilton, I. D. Utuk, M. Paneque-Sosa, M. Lopez-Poveda, J. Chem. Soc. Dalton Trans. 1989, 489; D. Morton, D. Cole-Hamilton, J. Chem. Soc. Chem. Commun. 1988, 1154; and D. Morton, D. J. Cole-Hamilton, J. Chem. Soc. Chem. Commun. 1987, 248). In the recent years, several new homogeneous catalysts for acceptorless dehydrogenative coupling of primary alcohols have been developed and studied, such as the systems published by Milstein and co-workers (for a review see: D. Milstein, Top. Catal. 2010, 53, 915) and Beller (Angew. Chem., Int. Ed. 2012, 51, 5711). However, most of these catalysts, with the exception of Ru-MACHO, are inactive at temperatures below 100° C., for example, for converting ethanol and propanol to hydrogen and ethyl acetate and propyl propionate, respectively.

Therefore, there remains a need for efficient and practical metal catalysts for the hydrogenation of esters, lactones, and fats and oils derived from natural sources, which can operate under base-free conditions and require relatively low reaction temperature and hydrogen pressure. There also remains a need for practical catalysts capable of efficient alcohol dehydrogenation under mild, and preferably neutral, reaction conditions, for environmentally benign production of esters and lactones from alcohols and diols, accompanied by formation of hydrogen gas.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide complex catalysts based on amino-sulfide ligands for hydrogenation and dehydrogenation processes. In accordance with one aspect of the present application there is provided a metal complex of Formula II and III

  II

  III wherein:

each Z is simultaneously or independently a hydrogen or halogen atom, a $C_1$-$C_6$ alkyl, a carbene group, a hydroxyl group, or a $C_1$-$C_7$ alkoxy radical, a nitrosyl (NO) group, CO, CNR (R=Alkyl, Aryl), nitrile, phosphite, phosphinite, or phosphine such as $PMe_3$ or $PPh_3$;

M is a transition metal; preferably from group 6, in which Ru and Os are particularly more preferable;

p is equal to 1 or 2, whereas a is equal to 1, 2, or 3;

SN and SNS are coordinated ligands of any one of Formulae IA,B:

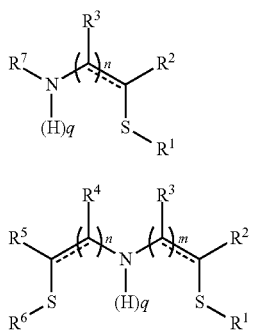

where
SR$^1$ is a thioether group, which is coordinated to the metal center of the catalyst or pre-catalyst;

the dotted lines simultaneously or independently indicate single or double bonds;

R$^1$, R$^2$, R$^5$, and R$^6$ are each independently H, a substituted or unsubstituted linear or branched C$_1$-C$_{20}$ alkyl (such as a C$_1$-C$_8$ alkyl), a substituted or unsubstituted cyclic C$_3$-C$_8$ alkyl, or a substituted or unsubstituted alkenyl, a substituted or unsubstituted C$_5$-C$_{20}$ aryl (such as a C$_5$-C$_{14}$ or C$_5$-C$_8$ aryl), OR or NR$_2$; or when taken together, R$^1$ and R$^2$ groups or R$^5$ and R$^6$ groups can form a saturated or partially saturated cycle;

R$^3$ and R$^4$ are each independently H, a substituted or unsubstituted linear, branched or cyclic C$_1$-C$_8$ alkyl or alkenyl, a substituted or unsubstituted C$_5$-C$_8$ aromatic group, ester group; or, when taken together, R$^3$ and R$^4$ can form an optionally substituted saturated or partially saturated hetero-aromatic ring;

R$^5$ when taken together with R$^4$ can form an optionally substituted saturated or partially saturated aromatic ring;

R$^7$ is H, a substituted or unsubstituted linear or branched C$_1$-C$_8$ alkyl (such as a C$_1$-C$_8$ alkyl), a substituted or unsubstituted cyclic C$_3$-C$_8$ alkyl, a substituted or unsubstituted alkenyl, or a substituted or unsubstituted C$_5$-C$_{20}$ aryl (such as a C$_5$-C$_{14}$ or C$_5$-C$_8$ aryl); and n, m, and q are simultaneously or independently 0, 1, or 2.

In accordance with another aspect there is provided a process for dehydrogenation of a substrate comprising: treating the substrate with a catalytic amount of a metal complex of Formula II and III $$M(SN)_pZ_a \quad \text{II}$$

$$M(SNS)Z_a \quad \text{III}$$

as defined above.

In accordance with another aspect there is provided a process for hydrogenation of a substrate comprising: treating the substrate under a pressure of hydrogen with a catalytic amount of a metal complex of Formula II and III $$M(SN)_pZ_a \quad \text{II}$$

$$M(SNS)Z_a \quad \text{III}$$

as defined above.

In accordance with certain embodiments, the metal complex comprises M that is a group 7 metal, a group 8 metal or a group 9 metal, for example, Ru or Os.

BRIEF DESCRIPTION OF THE FIGURES

For a better understanding of the present invention, as well as other aspects and further features thereof, reference is made to the following description which is to be used in conjunction with the accompanying drawings, where.

DESCRIPTION OF THE INVENTION

Figure 1:
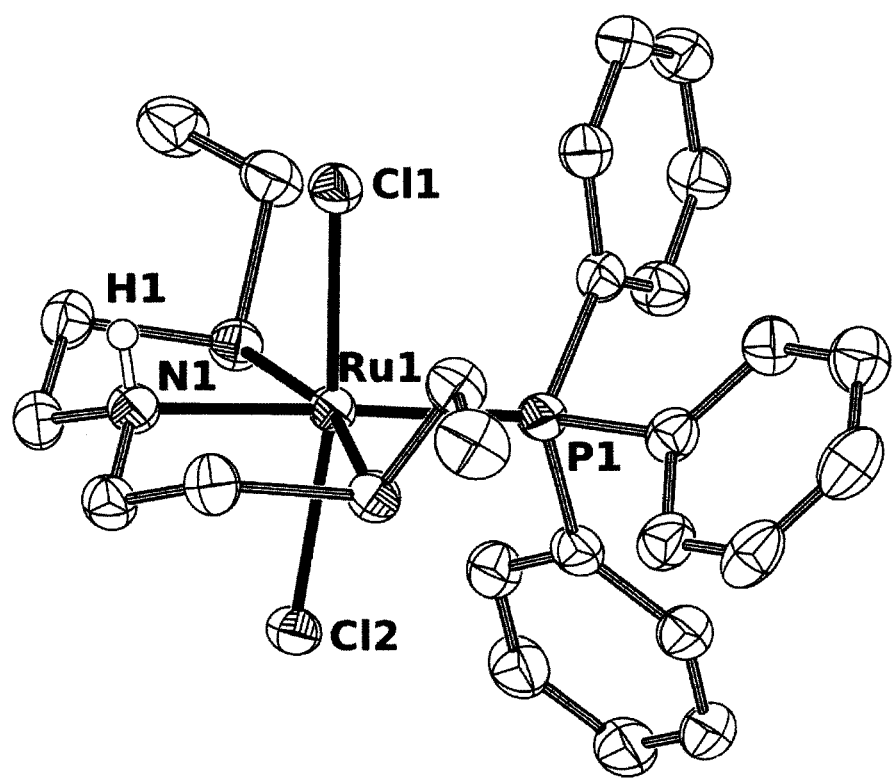
FIG. 1 is an ORTEP diagram for complex 1 (Example 5), thermal ellipsoids are at 50% probability (the hydrogen atoms are omitted for clarity)
Figure 2:
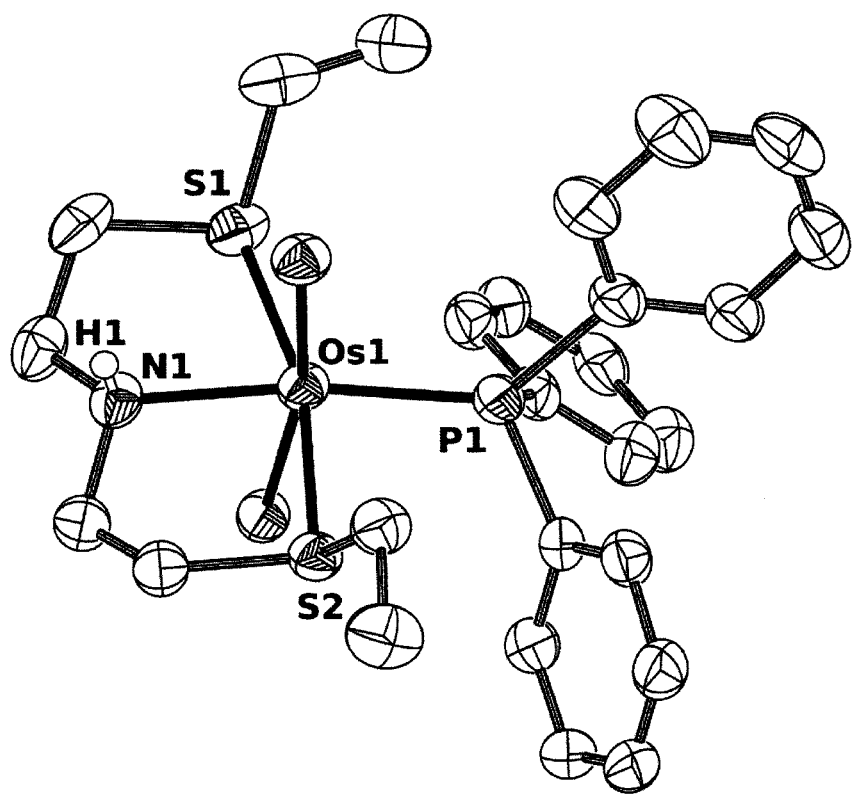
FIG. 2 is an ORTEP diagram for complex 2 (Example 6), thermal ellipsoids are at 50% probability (the hydrogen atoms are omitted for clarity)

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "heteroatom" refers to non-hydrogen and non-carbon atoms, such as, for example, O, S, and N.

As used herein, "alkyl" means a hydrocarbon moiety that consists solely of single-bonded carbon and hydrogen atoms, for example a methyl or ethyl group.

As used herein, "alkenyl" means a hydrocarbon moiety that is linear, branched or cyclic and comprises at least one carbon to carbon double bond. "Alkynyl" means a hydrocarbon moiety that is linear, branched or cyclic and comprises at least one carbon to carbon triple bond. "Aryl" means a moiety including a substituted or unsubstituted aromatic ring, including heteroaryl moieties and moieties with more than one conjugated aromatic ring; optionally it may also include one or more non-aromatic ring. "C$_5$ to C$_8$ Aryl" means a moiety including a substituted or unsubstituted aromatic ring having from 5 to 8 carbon atoms in one or more conjugated aromatic rings. Examples of aryl moieties include phenyl.

"Heteroaryl" means a moiety including a substituted or unsubstituted aromatic ring having from 4 to 8 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, furanyl and thienyl.

"Alkylene" means a divalent alkyl radical, e.g., —C$_f$H$_{2f}$— wherein f is an integer. "Alkenylene" means a divalent alkenyl radical, e.g., —CHCH—.] "Substituted" means having one or more substituent moieties whose presence does not interfere with the desired reaction. Examples of substituents include alkyl, alkenyl, alkynyl, aryl, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, aryl-halide and heteroarylcycloalkyl (non-aromatic ring).

The present application provides catalysts that are useful in catalytic hydrogenation (reduction) processes. The hydrogenation process is useful in hydrogenation of, for example, $C_2$-$C_n$ (n=3-200) substrates possessing one or more ester or lactone groups to afford the corresponding alcohol, diol, or triol products. Thus, the present application further provides a practical reduction method that can be used in place of the main-group hydride reduction to obtain alcohols, diols, or triols in a simple, efficient, and "green" fashion. The catalyst of the present application is also useful in catalytic dehydrogenation process, which can be, for example, a homogeneous dehydrogenation process.

Catalyst

The processes described herein are carried out in the presence of a catalyst or a pre-catalyst in the form of a transition metal complex of tridentate SNS or bidentate SN amino-sulfide ligands. The transition metal is preferably a metal from groups 7 (manganese group), 8 (iron group), and 9 (cobalt group), in which Ru and Os are particularly preferable.

The coordinating groups of the tridentate SNS ligand consist of two thioether groups and one nitrogen (amino) group. The coordinating groups of a bidentate SN ligand consist of one thioether and one nitrogen (amino) group. The general structure of the SN ligand is represented by Formula IA and the structure of the SNS ligand is represented by Formula IB.

Formula IA

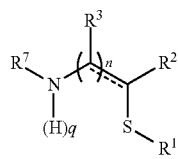

Formula IB

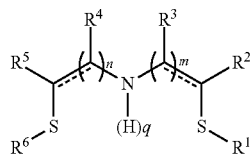

where $SR^1$ is a thioether group, which is coordinated to the metal center of the catalyst or pre-catalyst;

the dotted lines simultaneously or independently indicate single or double bonds;

$R^1$, $R^2$, $R^5$, and $R^6$ are each independently H, a substituted or unsubstituted linear or branched $C_1$-$C_{20}$ alkyl (such as a $C_1$-$C_8$ alkyl), a substituted or unsubstituted cyclic $C_3$-$C_8$ alkyl, or a substituted or unsubstituted alkenyl, a substituted or unsubstituted $C_5$-$C_{20}$ aryl (such as a $C_5$-$C_{14}$ or $C_5$-$C_8$ aryl), OR or $NR_2$; or when taken together, $R^1$ and $R^2$ groups or $R^5$ and $R^6$ groups can form a saturated or partially saturated cycle;

$R^3$ and $R^4$ are each independently H, a substituted or unsubstituted linear, branched or cyclic $C_1$-$C_8$ alkyl or alkenyl, a substituted or unsubstituted $C_5$-$C_8$ aromatic group, ester group; or, when taken together, $R^3$ and $R^4$ can form an optionally substituted saturated or partially saturated hetero-aromatic ring;

$R^5$ when taken together with $R^4$ can form an optionally substituted saturated or partially saturated aromatic ring;

$R^7$ is H, a substituted or unsubstituted linear or branched $C_1$-$C_8$ alkyl (such as a $C_1$-$C_8$ alkyl), a substituted or unsubstituted cyclic $C_3$-$C_8$ alkyl, a substituted or unsubstituted alkenyl, or a substituted or unsubstituted $C_5$-$C_{20}$ aryl (such as a $C_5$-$C_{14}$ or $C_5$-$C_8$ aryl); and n, m, and q are simultaneously or independently 0, 1, or 2.

The SN and SNS ligands can be synthesized using standard procedures which are well known in the art and by the person skilled in the art. For example, SN (IA) and SNS (IB) ligands can be obtained by alkylation of a mercaptane by 2-chloro-ethylamine hydrochloride or bis-(2-chloroethyl) amine hydrochloride, respectively, under basic conditions.

According to one embodiment of the invention, the catalyst or pre-catalyst is a metal complex of the general Formulae II-III:

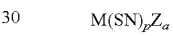

wherein SN is the bidentate ligand of Formula IA; a is 1, 2 or 3; p is 1 or 2; SNS is the tridentate ligand of Formula IB; and each Z represents simultaneously or independently a hydrogen or halogen atom, a $C_1$-$C_6$ alkyl radical, a carbene group, a hydroxyl group, or a $C_1$-$C_7$ alkoxy radical, a nitrosyl (NO) group, CO, CNR (R=Alkyl, Aryl), nitrile, phosphite, phosphinite, or phosphine such as $PMe_3$ or $PPh_3$. The catalysts and pre-catalysts can exist in both neutral and cationic forms. The transition metal M is preferably a metal from groups 7 (manganese group), 8 (iron group), and 9 (cobalt group), in which Ru and Os are particularly preferable.

In one embodiment, the catalyst has the following structure:

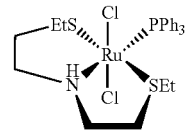

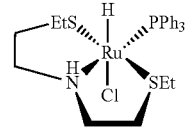

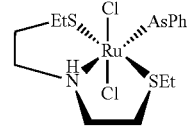

-continued

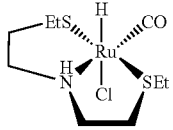

or the corresponding complex in with the Ru is replaced with Os.

In one embodiment, the complexes of Formulae II-III can be prepared by reaction of the ligands of Formulae IA, or IB with a metal precursor, such as those well known in the state of the art. Preferably, the metal precursor is a ruthenium or osmium compound, including, for example, a compound of the following formulae: $RuCl_2(AsPh_3)_3$, $RuHCl(AsPh_3)_3$, $RuCl_2(PPh_3)_3$, $RuHCl(PPh_3)_3$, $RuCl_2(CO)(PPh_3)_3$, $RuCl_2(CO)(AsPh_3)_3$, $RuHCl(CO)(AsPh_3)_3$, $OsHCl(AsPh_3)_3$, $OsCl_2(AsPh_3)_3$, $OsHCl(PPh_3)_3$, $OsCl_2(PPh_3)_3$, $[RuCl_2(p\text{-cymene})]_2$, $[OsCl_2(p\text{-cymene})]_2$, $RuCl_2(CO)(p\text{-cymene})$, $OsCl_2(CO)(p\text{-cymene})$, $RuCl_2(CO)(DMF)(PPh_3)_2$, $[IrCl(COD)]_2$, $[IrCl(COE)_2]_2$, $IrHCl_2(PPh_3)_3$, $IrH_2Cl(PPh_3)_3$, $IrHCl_2(AsPh_3)_3$, or $IrH_2Cl(AsPh_3)_3$. The reactions can be conducted in various organic solvents, such as, but not limited to, toluene, xylene, benzene, diglyme, DMF or DME.

Hydrogenation Process

The present application additionally provides a catalytic hydrogenation process. The catalyst complexes of Formulae II-III described above, have been shown to have high reactivity in reduction of the polar C=X (X=N, O) bonds. For examples, esters, ketones, fats, esters with multiple ester groups and imines can be mentioned.

In one embodiment, there is provided a process for hydrogenation of esters using metal catalysts based on the SNS ligand of Formula IB. The ester substrates are compounds of the following formulae:

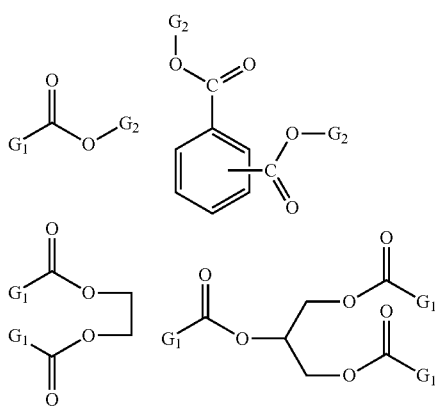

The term "substrate", as used herein, and as commonly understood by those of skill in the art, refers to the reactant that will be converted to a product during a catalytic reaction. Groups G1 and G2, simultaneously or independently, represent a linear, branched $C_1$-$C_{40}$ or cyclic $C_3$-$C_{40}$ alkyl, alkenyl or aromatic group, optionally substituted. Also contemplated herein is a situation when G1 and G2 together form a $C_4$-$C_{40}$ saturated or unsaturated radical. The substrate of the hydrogenation reaction can be any organic compound containing one, or more than one, carboalkoxy group or C=X (X=O, N) bond. In this respect, natural fats such as olive, canola, corn, peanut, palm and other plant oils are useful substrates that can be reduced to form a mixture of alcohols. Imines can be reduced to amines and ketones to secondary alcohols.

The reduction reaction proceeds, generally, according to the reaction scheme below:

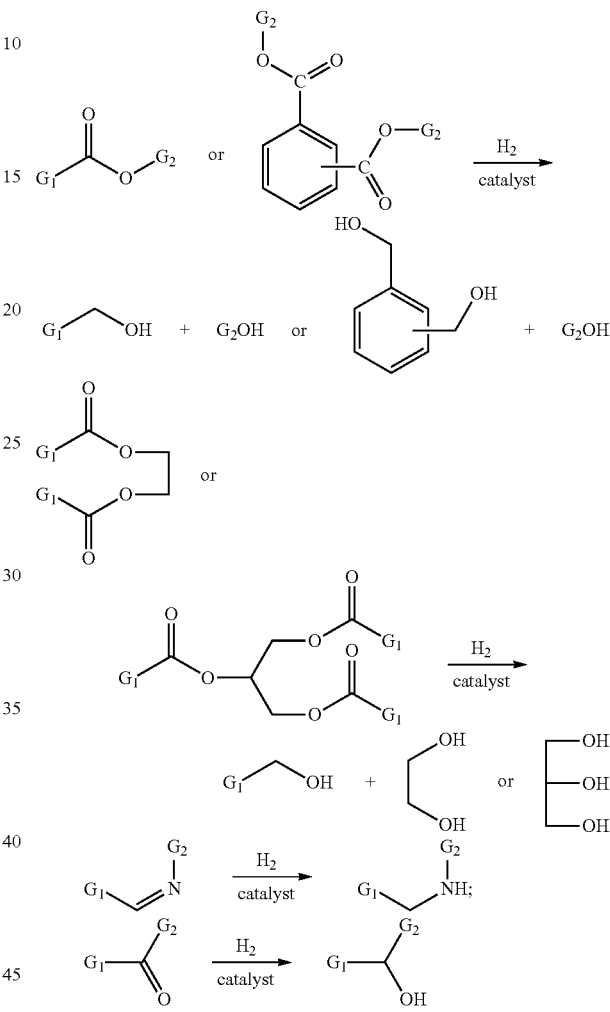

When the substrate is a monoester or a lactone, the products are alcohols or a diol, respectively. The naturally occurring triglycerides, oils and fats, can be reduced to glycerol and the corresponding fatty alcohols. Substrates with multiple ester groups, like phthalates, are reduced to diols and polyols. When the substrates are imines or ketones, the products are secondary amines and alcohols, respectively.

According to one embodiment, the process of catalytic reduction of imines and esters implies the usage of at least one of the metal complexes II or III, hydrogen pressure, and optionally a base and a solvent. The base may be necessary in those cases when the metal catalyst III contains one or more halogen atoms bonded to the metal. The treatment with base can be done prior to the reduction or in situ by adding base to the reaction mixture during hydrogenation. The catalysts and pre-catalysts of this invention can be used in a wide range of concentrations, preferably between about 10 and about 1000 ppm, and the loadings of 500 ppm or less are particularly preferred. The preferred amount of the catalyst will depend, as it is known to the person skilled in the art, on the type of the substrate, and increasing the catalyst loading may result in faster hydrogenation. The temperature at which the hydrogenation can be carried out is between about 0° C. and about 150° C., more preferably in the range between about 20° C. and about 100° C. and, as it is known to the person skilled in the art, the reaction rate will increase with an increase of the reaction temperature. The hydrogenation reaction requires a pressure of $H_2$ gas and should be performed in a suitable pressure vessel. The surface area of the reactor as well as the hydrogen pressure, as it is known to the person skilled in the art, can greatly influence the reaction rate. The greater the hydrogen pressure and/or the surface area of the reactor, the faster the hydrogenation reaction rate. In one embodiment the hydrogen pressure is in range of about 5 to about 200 Bar. Again, the person skilled in the art is well able to adjust the pressure as a function of the catalyst load and of the dilution of the substrate in the solvent. Examples of typical pressures used in the present hydrogenation reactions are from about 5 to about 50 bar (5 to 50×10⁵ Pa).

It should be well understood, however, that the catalyst complexes described herein are also useful in catalyzing hydrogenation of substrates including functional groups other than esters and imines. The table below provides a non-limiting list of substrates and products that can be formed from a catalytic hydrogenation reaction using a catalyst of Formula II or III.

| Hydrogenation Substrate | Product |
| --- | --- |
| aldehyde | alcohol |
| ketone | alcohol |
| ester | alcohol |
| carboxylic acid | alcohol |
| ketene | alcohol |
| enol | alcohol |
| epoxide | alcohol |
| aldimine | amine |
| ketimine | amine |
| ketene-imine | amine |
| nitrile | amine |
| aziridine | amine |
| nitro | amine |
| diazo | amine |
| isocyanide | amine |
| enamine | amine |
| lactone | diol |
| amide | amine + alcohol |
| aminoboranes | amine-borane |
| borazine | amine-borane |
| olefin | alkane |
| acetylene | alkane |
| allene | alkane |

Dehydrogenation Reaction

The present application further provides a process of catalytic dehydrogenation using the catalyst complexes of Formulae II and III. For example, these catalysts or pre-catalysts are suitable for dehydrogenation of $C_n$ (n=2-200) alcohols possessing one or more —$CH_2OH$ groups thereby affording hydrogen gas and the corresponding esters or lactones. The substrates are compounds of the following formulae:

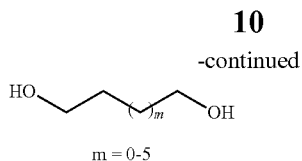

R = $C_1$-$C_n$ alkyl or ary substituents (optionally substituted)

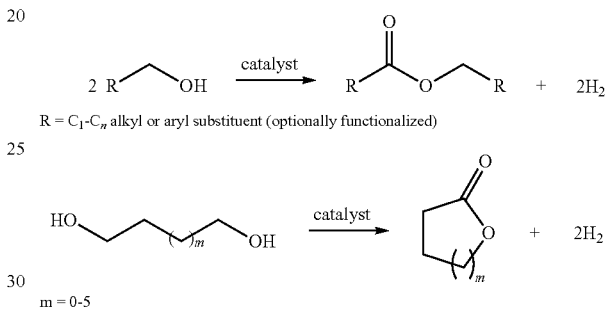

m = 0-5

In this embodiment, R groups, simultaneously or independently, represent a linear, branched $C_1$-$C_{40}$ or cyclic $C_3$-$C_{40}$ alkyl, alkenyl or aromatic group, optionally substituted. Also contemplated herein is the situation when R is a $C_4$-$C_{40}$ saturated or unsaturated cyclic radical. This implies that the substrate can be any organic compound containing one, or more than one, hydroxyl (OH) group.

The reduction process of this embodiment is illustrated below. When the substrate is an alcohol or a diol, the product is an ester or a lactone, respectively.

$$2\,R\!-\!\!\diagup\!\!\diagdown\!\!OH \xrightarrow{\text{catalyst}} R\!-\!\!\overset{\overset{O}{\|}}{C}\!\!-\!O\!-\!\!\diagup\!\!\diagdown\!\!R + 2H_2$$

R = $C_1$-$C_n$ alkyl or aryl substituent (optionally functionalized)

$$HO\!\!\diagup\!\!\diagdown\!\!(\,)_m\!OH \xrightarrow{\text{catalyst}} \text{lactone} + 2H_2$$

m = 0-5

According to one embodiment, the process of catalytic acceptorless dehydrogenation implies the usage of at least one of the metal complexes of Formulae II or III and (optionally) the use of a base and a solvent. The base may be necessary in those cases when the metal catalyst of Formula II or III contains one or more halogen or alkoxy (—OR) groups bonded to the metal. The catalyst can be treated with base prior to mixing with the substrate or in situ by adding base to the reaction mixture during dehydrogenation. The catalysts and pre-catalysts described herein can be used in a wide range of concentrations, preferably between about 10 and about 1000 ppm, and the loadings of 1000 ppm or less are particularly preferred. The preferred amount of the catalyst will depend, as it is known to the person skilled in the art, on the type of the substrate; and increasing the catalyst loading should result in faster dehydrogenation. The temperature at which the dehydrogenation can be carried out is between about 0° C. and about 200° C., more preferably in the range between about 50° C. and about 150° C. and, as it is known to the person skilled in the art, the reaction rate will increase with increase of the reaction temperature. The dehydrogenation process can generate a pressure of $H_2$ gas and, in such cases, can be performed in a suitable pressure vessel that is, if necessary, equipped with a pressure-release valve.

It should be well understood, however, that the catalyst complexes described herein are also useful in catalyzing dehydrogenation of substrates including functional groups other than alcohols. The table below provides a non-limiting list of substrates and products that can be formed from a catalytic dehydrogenation reaction using a catalyst of Formula II or III.

| Substrate | Product[a] |
|---|---|
| alcohols | ester |
| alcohol | aldehyde |
| alcohol | ketone |
| diol | lactone |
| amine + alcohol | amide |
| amine + alcohol | substituted amine |
| amine + alcohol | imine |
| ammonia-borane | aminoboranes |
| ammonia-borane | borazine |
| amine | imine |
| amines | guanidine |
| alcohol + thiol | thioester |
| thiol | sulphoxide |
| alcohol + phosphine | acyl phosphine |

[a]$H_2$ is also a byproduct of these reactions. It is either liberated from the reaction as $H_2$ or transferred to an acceptor.

As noted above, a byproduct of the dehydrogenation reactions is $H_2$. Accordingly, the present application further provides a process for producing $H_2$. The process can conveniently make use of readily available substrates in a straightforward catalytic dehydrogenation process under relatively mild conditions to generate $H_2$.

To gain a better understanding of the invention described herein, the following examples are set forth. It should be understood that these examples are for illustrative purposes only. Therefore, they should not limit the scope of this invention in any way.

EXAMPLES

Unless mentioned otherwise, all manipulations have been performed under an atmosphere of argon in a glove box, or using standard Schlenk techniques. NMR spectra were recorded on a Varian Unity Inova 300 MHz spectrometer. All 31P chemical shifts are relative to 85% $H_3PO_4$. 1H and 13C chemical shifts were measured relative to the solvent peaks but they are reported relative to TMS. $RuCl_3 \cdot 3H_2O$ was purchased from Pressure Chemicals. Ru-MACHO (VI), $RuCl_2(Ph_2PC_2H_4NH_2)_2$ (V), and Milstein's catalyst III were purchased from Strem Chemicals. All other compounds and anhydrous grade solvents were obtained from Aldrich and Alfa Aesar. Commercial anhydrous grade ethanol was further distilled over sodium metal and stored in the argon glovebox. $RuHCl(CO)(AsPh_3)_3$ [D. Spasyuk, S. Smith, D. G. Gusev, *Angew. Chem.* 2012, 51, 2772-2775] and $RuCl_2(PPh_3)_3$ [S. Rajagopal, S. Vancheesan, J. Rajaram, J. C. Kuriacose, *J. Mol. Cat.* 1983, 22, 131-135] were prepared according to previously reported methods.

Example 1. Synthesis of $EtS(CH_2)_2NH_2$

All manipulations were carried in air. In a 250 mL flask, 24 g (0.191 mol) of NaOH was dissolved in 100 mL of $CH_3OH$ and EtSH (15 g, 0.242 mol) was added. After 10 minutes of reaction, 28.07 g (0.242 mol) of 2-chloroethylamine hydrochloride was slowly added to the mixture and the reaction was left to stir overnight. In the following morning, methanol was removed in vacuo and the remaining semisolid was extracted with 3×30 mL of $Et_2O$. The obtained extract was filtered through a short plug (2 cm×1 cm) of $Al_2O_3$ and ether was removed under reduced pressure (15 mm Hg) to yield a pale yellow oil (23.4 g, 92%).

$^1H$ NMR ([D6]Benzene) δ=2.54 (t, J=6.2 Hz, 2H, $CH_2$), 2.25 (t, J=6.2 Hz, 2H, $CH_2$), 2.18 (q, J=7.4 Hz, 2H, $SCH_2$), 1.02 (t, J=7.4 Hz, 3H, $CH_3$), 0.76 (br, 2H, $NH_2$). $^{13}C\{^1H\}$ NMR ([D6]Benzene) δ=41.72 (s, 1C, $NCH_2$), 36.22 (s, 1C, $CH_2S$), 25.72 (s, 1C, $SCH_2$), 15.11 (s, 1C, $CH_3$).

Example 2. Synthesis of $(EtS(CH_2)_2)_2NH$

All manipulations were carried in air. To a solution of bis(2-chloroethyl)amine hydrochloride (23.9 g, 0.134 mol) in 80 mL of methanol were added NaOH (6.27 g, 0.157 mol) and sodium ethanethiolate (25 g, 0.298 mol). The resulting mixture was stirred overnight at room temperature. After that time, methanol was removed in vacuo. The remaining yellow slurry was extracted with 3×15 mL of $Et_2O$ and the obtained extract was filtered through a short plug (2 cm×1 cm) of $Al_2O_3$. The solvent was removed in vacuo to yield a pale yellow oil (23.0 g, 89%).

Alternatively, $(EtS(CH_2)_2)_2NH$ was prepared by the following, slightly different method. Again all manipulations were performed in air. To a solution of NaOH (6.27 g, 0.157 mol) and sodium ethanethiolate (25 g, 0.298 mol) in 80 mL of methanol was slowly added bis(2-chloroethyl)amine hydrochloride (23.9 g, 0.134 mol) in 65 ml of methanol. The mixture was stirred overnight at room temperature, and then the solvent was removed under reduced pressure. The resulting yellow slurry was extracted with 3×20 mL of hexane and the obtained extract was filtered through a short plug (2×1 cm) of basic alumina. The solvent was evaporated to give a pale yellow oil with the same yield as above (23.0 g, 89%).

$^1H$ NMR ([D6]Benzene) δ=2.62 (t, J=6.6 Hz, 4H, 2×$NCH_2$), 2.46 (t, J=6.5 Hz, 4H, 2×$SCH_2$), 2.27 (q, J=7.4 Hz, 4H, 2×$SCH_2$), 1.42 (br, 1H, NH), 1.06 (t, J=7.4 Hz, 6H, 2×$CH_3$). $^{13}C\{^1H\}$ NMR ([D6]Benzene) δ=49.04 (s, 2C, 2×$NCH_2$), 32.50 (s, 2C, 2×$CH_2S$), 26.03 (s, 2C, 2×$SCH_2$), 15.15 (s, 2C, 2×$CH_3$).

Example 3. Synthesis of $(EtSC_2H_4)_2O$

All manipulations were performed in air. To a solution of NaSEt (5.41 g, 64.4 mmol) in 40 mL of methanol was added a solution of bis(2-chloroethyl) ether (4.6 g, 32.2 mmol) in 20 mL of methanol. The mixture was stirred overnight at 40° C., and then the solvent was removed under reduced pressure. The resulting slurry was extracted with 2×20 mL of hexanes and the obtained extract was filtered through a short plug (2×1 cm) of basic alumina. The solvent was evaporated to give a transparent oil (4.07 g, 64%). $^1H$ NMR ([D6]Benzene) δ 3.39 (t, J=6.9 Hz, 4H, $OCH_2$), 2.52 (t, J=6.9 Hz, 4H, $CH_2S$), 2.31 (q, J=7.4 Hz, 4H, $SCH_2$), 1.05 (t, J=7.4 Hz, 6H, $CH_3$). $^{13}C\{1H\}$ NMR ([D6]Benzene) δ 71.38 (s, 2C, $CH_2O$), 31.50 (s, 2C, $CH_2S$), 26.66 (s, 2C, $SCH_2$), 15.13 (s, 2C, $CH_3$).

Example 4. Synthesis of $(EtSC_2H_4)_2NMe$

All manipulations were performed in air. A mixture of $(EtS(CH_2)_2)_2NH$ (500 mg, 2.59 mmol), formic acid (477 mg, 10.36 mmol) and 1 mL of formaldehyde (40% in water) was refluxed for 2 h. The reaction mixture was cooled, treated with 10 mL of a 20% aqueous solution of NaOH and extracted with 3×10 mL of $Et_2O$. The combined ether solution was washed with 2×10 mL of water and evaporated under vacuum. The residue was further dried under vacuum at 50° C. The product was isolated as a transparent oil. Yield: 397 mg (65%). $^1H$ NMR ([D]Chloroform) δ 2.65-2.59 (m, 8H, $CH_2$), 2.54 (q, J=7.4 Hz, 4H, $SCH_2$), 2.28 (s, 3H, $NCH_3$), 1.25 (t, J=7.4 Hz, 6H, $CH_3$). $^{13}C\{1H\}$ NMR ([D]

Chloroform) δ 57.49 (s, NCH$_2$), 42.15 (s, NCH$_3$), 29.30 (s, CH$_2$S), 26.29 (s, SCH$_2$), 14.98 (s, CH$_3$).

Example 5. Synthesis of RuCl$_2$(PPh$_3$)[(EtS(CH$_2$)$_2$)$_2$NH], (1)

A 100 mL Schlenk flask containing a mixture of RuCl$_2$(PPh$_3$)$_3$ (5.00 g, 5.22 mmol) and (EtS(CH$_2$)$_2$)$_2$NH (1.01 g, 5.23 mmol) in 40 mL of toluene was heated at 100° C. for 2 h to get a yellow suspension. The product was filtered in air, washed with 10-15 mL of Et$_2$O giving a cream yellow solid which was dried under vacuum for 2 h. Yield: 2.98 g (91%). The compound was isolated as a mixture of three isomers differing by the relative orientation of the SEt groups with respect to the SNS ligand plane. The synthesis was repeated using a mixture of RuCl$_2$(PPh$_3$)$_3$ (15.00 g, 15.66 mmol) and (EtS(CH$_2$)$_2$)$_2$NH (3.03 g, 15.7 mmol) in 50 mL of toluene. The yield was 8.64 g (88%) and the product was again isolated as a mixture of the three isomers differing by the relative orientation of the SEt groups with respect to the SNS ligand plane. $^1$H{$^{31}$P} NMR ([D2]DCM) δ 7.70-7.38 (m), 7.40-6.95 (m), 5.21 (br, NH), 4.99 (br, NH), 4.61 (br, NH), 3.25 (m), 3.06 (m), 2.97-2.58 (m), 2.46-2.24 (m), 1.71-1.39 (m), 1.03 (t, J=7.0 Hz, CH$_3$), 1.04 (t, J=7.0 Hz, CH$_3$). $^{13}$C{$^1$H} NMR ([D2]DCM) δ$_{major\ isomer}$=137.42 (d, J(CP)=39.3 Hz, 3C, {PAr}C$^{ipso}$), 134.87 (d, J(CP)=10.0 Hz, 6C, {PAr}C$^{ortho}$), 129.46 (d, J(CP)=6.7 Hz, 3C, {PAr}C$^{para}$), 127.91 (d, J(CP)=9.4 Hz, 6C, {PAr}C$^{meta}$), 49.24 (s, 2C, 2×NCH$_2$), 39.81 (s, 2C, 2×CH$_2$S), 29.96 (s, 2C, 2×SCH$_2$), 13.23 (s, 2C, 2×CH$_3$). $^{31}$P{$^1$H} NMR ([D2]DCM) δ=51.08 (major isomer, s, 1P), 49.51 (minor isomer, br. s, 1P), 48.02 (minor isomer, br. s, 1P).

Example 6. Synthesis of OsCl$_2$(PPh$_3$)[(EtS(CH$_2$)$_2$)$_2$NH] (2)

A 50 mL Schlenk flask containing a mixture of OsCl$_2$(PPh$_3$)$_3$ (3.00 g, 3.07 mmol) and (EtS(CH$_2$)$_2$)$_2$NH (0.594 g, 3.07 mmol) in 25 mL of toluene was heated at 100° C. for 2 h to get a yellow suspension. The product was filtered in air, washed with 10-15 mL of Et$_2$O giving an orange solid which was dried under vacuum for 2 h. Yield: 1.91 g (87%). The compound was isolated as a mixture of 3 isomers differing by the relative orientation of the SEt groups with respect to the SNS ligand plane. $^1$H{$^{31}$P} NMR ([D2]DCM) δ$_{sum}$ 7.70-7.38 (m), 7.40-6.95 (m), 5.21 (br, NH), 4.99 (br, NH), 4.61 (br, NH), 3.25 (m), 3.06 (m), 2.97-2.58 (m), 2.46-2.24 (m), 1.71-1.39 (m), 1.04 (t, J=7.0 Hz, CH$_3$), 0.936 (br, CH$_3$). $^{13}$C{$^1$H} NMR ([D2]DCM) δ$_{major\ isomer}$=139.20 (d, J(CP)=46.3 Hz, 3C, {ArP}C$^{ipso}$), 134.72 (d, J(CP)=9.9 Hz, 6C, {ArP}C$^{meta}$), 129.34 (d, J(CP)=7.9 Hz, 3C, {ArP}C$^{para}$), 127.86 (d, J(CP)=9.3 Hz, 6C, {ArP}C$^{meta}$), 50.14 (s, 2C, 2×NCH$_2$), 40.27 (s, 2C, 2×CH$_2$S), 30.81 (s, 2C, 2×SCH$_2$), 12.99 (s, 2C, 2×CH$_3$). $^{31}$P{$^1$H} NMR ([D2]DCM) δ=2.00 (major isomer, s, 1P), −0.23 (minor isomer, br. s, 1P), −2.35 (minor isomer, br. s, 1P).

Example 7. Synthesis of RuHCl(PPh$_3$)[(EtS(CH$_2$)$_2$)$_2$NH], (3)

A 100 mL Schlenk flask containing a mixture of RuHCl(PPh$_3$)$_3$ (4.80 g, 5.20 mmol) and (EtSC$_2$H$_4$)$_2$NH (1.01 g, 5.23 mmol) in 30 mL of toluene was heated at 100° C. for 2 h to form a dark-green solution. Diethyl ether (10 mL) was added and the product was left to crystallize in a freezer. The precipitate was filtered, washed with 20 mL of ether to give a dark-green solid which was dried under vacuum for 2 h.

Yield: 1.97 g (64%). The product was isolated as a mixture of 3 isomers differing by the relative orientation of the SEt groups with respect to the SNS ligand plane. $^1$H NMR ([D2]DCM) δ 8.04-7.39 (m, {Ph}H$^{ortho}$), 7.47-6.93 (m, {Ph}H$^{meta}$+{Ph}H$^{para}$), 4.79, 4.63, 4.21 (br, NH), 3.64-3.00 (m, CH$_2$), 3.07-2.48 (m, CH$_2$), 2.21-1.70 (m, CH$_2$), 0.84 (t, J(HH)=7.2 Hz, 2×CH$_3$), −20.16 (d, J(HP)=26.1 Hz RuH), −21.01 (d, J(HP)=25.4 Hz, RuH), −21.55 (d, J(HP)=27.4 Hz, RuH). $^{13}$C{$^1$H} NMR ([D2]DCM) of the major isomer, δ 140.35 (d, J(CP)=38.4 Hz, {Ph}C$^{ipso}$), 134.14 (d, J(CP)=11.0 Hz, {Ph}C$^{ortho}$), 128.55 (s, {Ph}C$^{para}$), 127.44 (d, J(CP)=8.9 Hz, {Ph}C$^{meta}$), 51.33 (s, NHCH$_2$), 37.35 (s, CH$_2$S), 36.24 (s, SCH$_2$), 13.94 (s, CH$_3$). $^{31}$P{$^1$H} NMR ([D2]DCM) δ 72.62 (s, 34%), 70.86 (s, 35%), 68.31 (s, 31%). Anal. Calcd for C$_{26}$H$_{35}$ClNPRuS$_2$: C, 52.64; H, 5.95; N, 2.36. Found: C, 52.35; H, 5.86; N, 1.81.

Example 8. Synthesis of RuCl$_2$(AsPh$_3$)[(EtS(CH$_2$)$_2$)$_2$NH]·Toluene, (4)

A 100 mL Schlenk flask containing a mixture of RuCl2(AsPh3)3 (2.24 g, 2.06 mmol) and (EtSC$_2$H$_4$)$_2$NH (400 mg, 2.06 mmol) in 20 mL of toluene was heated at 110° C. for 2 h to form a dark-grey suspension. The precipitate was filtered, washed with 15 mL of Et$_2$O to give a grey solid which was purified by recrystallization from THF/Et$_2$O in a freezer. Yield: 456 mg (33%). The compound was isolated as a mixture of 3 isomers differing by the relative orientation of the SEt groups with respect to the SNS ligand plane. $^1$H NMR ([D2]DCM) δ 7.75-7.47 (m, {Ph}H$^{ortho}$), 7.44-7.13 (m, {Ph}H$^{meta}$, {Ph}H$^{para}$, {Toluene}H), 4.92, 4.69, 4.48 (br, NH), 3.56-3.26 (m, CH$_2$), 3.32-2.57 (m, CH$_2$), 2.62-2.32 (m, CH$_2$), 2.12 (s, {Toluene}CH$_3$) 1.93-1.43 (m, CH$_2$), 1.14-0.91 (br overlapped t, J=7.3 Hz, CH$_3$). $^{13}$C {$^1$H} NMR ([D2]DCM) δ 137.46 (s, {Toluene}C$^{ipso}$), 134.23 (s, {AsPh}C$^{ipso}$), 134.12 (s, {AsPh}C$^{ortho}$), 129.17 (s, {AsPh}C$^{meta}$), 129.08 (s, {Toluene}C$^{ortho}$), 128.14 (s, {Toluene}C$^{meta}$), 128.02 (s, {AsPh}C$^{para}$), 125.32 (s, {Toluene}C$^{para}$), 49.66 (s, CH$_2$), 39.49 (s, CH$_2$), 30.39 (s, CH$_2$), 12.99 (s, CH$_3$). Anal. Calcd for C$_{26}$H$_{34}$Cl$_2$NRuAsS$_2$: C, 46.50; H, 5.10; N, 2.09. Found: C, 46.52; H, 4.98; N, 2.05.

Example 9. Synthesis of RuHCl(CO)[(EtSC$_2$H$_4$)$_2$NH] (5)

A 100 mL Schlenk flask containing a mixture of RuHCl(CO)(AsPh$_3$)$_3$ (5.61 g, 5.20 mmol) and (EtSC$_2$H$_4$)$_2$NH (1.00 g, 5.20 mmol) in 50 mL of toluene was refluxed for 3 h to form a dark-green suspension. The precipitate was filtered, washed with 15 mL of Et$_2$O to give a dark-green solid which was dried under vacuum for 2 h. Yield: 1.60 g (85%). The compound was isolated as a mixture of 3 isomers differing by the relative orientation of the SEt groups with respect to the SNS ligand plane. $^1$H{$^{31}$P} NMR ([D2]DCM) δ 4.28 (br, NH), 3.62-3.23 (m, 4H, CH$_2$), 3.11-2.25 (m, 8H, CH$_2$), 1.30 (t, J=7.3 Hz, CH$_3$), −16.84 (s, 28%, RuH), −17.14 (s, 51%, RuH), −17.48 (s, 21%, RuH). $^{13}$C {$^1$H} NMR ([D2]DCM) of the mixture of isomers, δ 205.01 (d, J(CH)=4.5 Hz, due to the residual coupling to the hydride, CO), 52.46 (s, CH$_2$), 52.39 (s, CH$_2$), 50.95 (s, CH$_2$), 50.82 (s, CH$_2$), 40.96 (s, CH$_2$), 40.57 (s, CH$_2$), 39.16 (s, CH$_2$), 32.64 (s, CH$_2$), 32.10 (s, CH$_2$), 13.25 (s, CH$_3$), 13.17 (s, CH$_3$), 13.13 (s, CH$_3$). Anal. Calcd for C$_9$H$_{20}$ClNORuS$_2$: C, 30.12; H, 5.62; N, 3.90. Found: C, 30.71; H, 5.48; N, 3.63.

Example 10. Synthesis of RuH(OEt)(PPh$_3$) [(EtSC$_2$H$_4$)$_2$NH].EtOH (6.EtOH)

A mixture of complex 1 (1.7 g, 2.71 mmol) and EtONa (553 mg, 8.13 mmol) in 30 mL of ethanol was refluxed for 1 h to give a yellow solution (Caution: vigorous H+ evolution!). The solvent was removed under reduced pressure (without heating) to give a highly air-sensitive yellow oil. The product was mixed with 20 mL of diethyl ether/toluene (3:1) and placed in a freezer for 1 h, then filtered through a glass frit, using 4-5 mL of hexane to wash the collected solids. The filtrate was evaporated under vacuum to dryness (without heating) to yield a yellow, air-sensitive solid. Yield: 1.32 g (75%). The compound was isolated as a mixture of 3 isomers differing by the relative orientation of the SEt groups with respect to the SNS ligand plane. $^1$H NMR ([D6]Benzene) δ 7.99 (m, {Ph}H$^{ortho}$), 7.59 (br, 2H, NH+OH), 7.10 (m, {Ph}H$^{meta}$+{Ph}H$^{para}$), 3.99 (br, 4H, OCH$_2$), 3.54-1.49 (m, 12H, CH$_2$), 1.44 (br, 6H, CH$_3$), 0.97--0.11 (br, 6H, CH$_3$), −20.30--21.73 (overlapped d, RuH). $^{31}$P{$^1$H} NMR ([D6]Benzene) δ minor isomers 70.44-69.00 (br. s), major isomer 69.00-67.49 (br. s). In the solid state, 5.EtOH rapidly changes color to black when exposed to air. No satisfactory elemental analysis could be obtained for 5.EtOH because of the sensitivity to air.

Example 11. Synthesis of RuH$_2$(PPh$_3$)[(EtSC$_2$H$_4$)$_2$NH] (7)

A solution of complex 6 (200 mg, 0.309 mmol, in 2 mL of benzene) was kept in an oil bath at 60° C. for 30 min, then moved in a refrigerator, at +3° C. The product crystallized and was isolated by filtration. It was briefly (25 min) dried under vacuum thus affording an air-sensitive, yellow solid (74 mg, 44%) as a single isomer. 1H NMR ([D8]THF) δ 8.38 (s, 1H, NH), 7.85 (m, 6H, {Ph}H$^{ortho}$), 7.25-6.97 (m, 9H, {Ph}Hmeta+{Ph}Hpara), 3.00-1.45 (overlapped br, 12H, CH$_2$), 0.84 (t, J(HH)=7.1 Hz, 6H, CH$_3$), −12.20 (d, J(HP)=27.9 Hz, 1H, RuH). 13C{1H} NMR ([D8]THF) δ 144.96 (d, J(CP)=33.0 Hz, 3C, {Ph}Cipso), 134.22 (d, J(CP)=11.2 Hz, 6C, {Ph}Cortho), 127.58 (s, 3C, {Ph}Cpara), 127.26 (d, 6C, J(CP)=8.5 Hz, {Ph}Cmeta), CH2 carbons were not observed due to line broadening, 14.33 (s, CH3). 31P{1H} NMR ([D8]THF) δ 82.00 (s). In the solid state, 7 rapidly changes color to black when exposed to air. No satisfactory elemental analysis could be obtained for 6 because of the sensitivity to air.

Example 12. Synthesis of RuCl$_2$(PPh$_3$)[(EtSC$_2$H$_4$)$_2$O] (8)

A 100 mL Schlenk flask containing a mixture of RuCl$_2$(PPh$_3$)$_3$ (4.93 g, 5.15 mmol) and (EtSC$_2$H$_4$)$_2$O (1.00 g, 5.15 mmol) in 40 mL of toluene was heated at 100° C. for 2 h to give a light-brown suspension. The product was filtered in air, washed with 15 mL of Et$_2$O affording a light-brown solid which was dried under vacuum for 2 h. Yield: 2.16 g (68%). The compound was isolated as a mixture of 2 isomers differing by the relative orientation of the Set groups with respect to the SOS ligand plane. $^1$H NMR ([D2]DCM) δ 7.83-7.48 (m, {Ph}H), 7.48-7.10 (m, {Ph}H), 4.40-4.18 (m, CH$_2$), 4.21-3.83 (m, CH$_2$), 3.32-3.01 (m, CH$_2$), 3.01-2.37 (m, CH$_2$), 1.76-1.37 (m, CH$_2$), 1.00 (t, J=6.8 Hz, 2×CH$_3$). $^{13}$C{$^1$H} NMR ([D2]DCM) δ major isomer 136.81 (d, J(CP)=45.2 Hz, {Ph}C$^{ipso}$), 134.84 (d, J(CP)=9.7 Hz, {Ph}C$^{ortho}$), 129.70 (s, {Ph}C$^{para}$), 127.82 (d, J(CP)=9.5 Hz, {Ph}C$^{meta}$), 69.80 (s, OCH$_2$), 36.99 (s, CH$_2$S), 27.59 (s, SCH$_2$), 12.92 (s, CH$_3$). $^{31}$P NMR ([D2]DCM) δ major isomer 62.32 (s), minor isomer 60.42 (s). Anal. Calcd for C$_{26}$H$_{34}$Cl$_2$ORuPS$_2$: C, 49.67; H, 5.29; S, 10.18. Found: C, 49.29; H, 5.18; S, 10.00.

Example 13. Synthesis of RuCl$_2$(PPh$_3$)[(EtSC$_2$H$_4$)$_2$NMe] (9)

A 50 mL Schlenk flask containing a mixture of RuCl$_2$(PPh$_3$)$_3$ (924 mg, 0.964 mmol) and (EtSC$_2$H$_4$)$_2$NMe (200 mg, 0.964 mmol) in 10 mL of toluene was heated at 110° C. for 2 h to give a yellow suspension. The product was filtered in air, washed with 3×5 mL of Et$_2$O affording a yellow solid which was dried under vacuum for 2 h. Yield: 407 mg (66%). $^1$H NMR ([D2]DCM) δ 7.97-7.62 (m, 6H, {PPh$_3$}H$^{ortho}$), 7.51-7.12 (m, 9H, {PPh$_3$}H$^{meta+para}$), 3.45 (m, CH$_2$), 3.17 (s, 3H, CH$_3$), 3.02 (m, 1H), 2.79 (m, 3H), 2.51 (m, 2H), 2.22 (m, 3H), 1.71 (m, 1H), 0.80 (overlapped, 6H, CH$_3$), 0.09 (m, 1H). $^{13}$C{$^1$H} NMR ([D2]DCM) δ 137.21 (d, J(CP)=41.4 Hz, {PPh$_3$}C$^{ipso}$), 135.08 (d, J(CP)=9.2 Hz, {PPh$_3$}C$^{ortho}$), 129.50 (s, {PPh$_3$}C$^{meta}$), 127.94 (d, J(CP)=9.1 Hz, {PPh$_3$}C$^{para}$), 60.55 (s, CH$_2$N), 58.91 (s, CH$_2$N), 50.97 (s, NCH$_3$), 36.40 (s, CH$_2$S), 33.50 (s, CH$_2$S), 29.37 (s, SCH$_2$), 27.64 (s, SCH$_2$), 13.09 (s, CH$_3$), 12.90 (s, CH$_3$). $^{31}$P NMR ([D2]DCM) δ 44.94 (s).

Example 13. Typical Procedure for Hydrogenation of Esters or Imines Using Complex 1

A solution of catalyst 1 in THF (3.2 mg/mL) and 1 mol % of a base was mixed together with 0.02 mol of a substrate (ester or imine) in 6 g of THF (or neat). The mixture was then transferred into a 75 mL stainless-steel reactor (Parr 4740) equipped with a magnetic stir bar. The reactor was purged by two cycles of pressurization/venting with H$_2$ (150 psi, 10 Bar) and then pressurized with H$_2$ (725 psi, 50 Bar) and disconnected from the H$_2$ source. The reaction was conducted for a predetermined length of time at 20-100° C. At the end of the reaction time, the reactor was placed into a cold water bath (if necessary) and it was depressurized after cooling to the ambient temperature.

Example 14. Hydrogenation of Methyl Benzoate Using Complex 1

1 mL of a THF solution of complex 1 (3.2 mg/mL, 0.025 mol %) was added to KOCH$_3$ (14 mg, 0.2 mmol). The obtained mixture was stirred for 1-2 min and then methyl benzoate (2.72 g, 20.0 mmol) in 5 mL of THF was added. The subsequent manipulations were carried out following the procedure in Example 13.

Example 15. Hydrogenation of Ethyl Acetate Using Complex 1 or Complex 2

1 mL of a THF solution of complex 1 (3.2 mg/mL, 0.0025 mol %) was added to NaOEt (136 mg, 2.0 mmol). The obtained mixture was stirred for 1-2 min and then ethyl acetate (17.6 g, 0.20 mol) was added. The subsequent manipulations were carried out following the procedure in Example 5 except that a 300 mL reactor was used and the reaction was conducted under a constant pressure of H$_2$ (50 Bar).

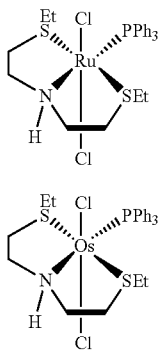

1

2

TABLE 2

Results of catalytic acceptorless dehydrogenation of ethanol to ethylacetate.

| Entry | Cat | S/C | t, h | Conversion to EtOAc, % |
|---|---|---|---|---|
| 1 | 1, Ru | 2000 | 16 | 97 |
| 2 | 1, Ru | 10000 | 24 | 89 |
| 3 | 1, Ru | 20000 | 43 | 36[b] |
| 4 | 2, Os | 2000 | 16 | 97 |
| 5 | 2, Os | 10000 | 24 | 81 |
| 6 | 2, Os | 20000 | 43 | 71[b] |
| 7 | 2, Os | 50000 | 43 | 54[b] |

[b]catalyst in solution of toluene was used.

TABLE 1

Hydrogenation of esters catalyzed by complexes 1, 2.

| Entry | Substrate | Cat | S/C | t, h | Solvent | Base, % | T, °C | Conv. (%)[a] |
|---|---|---|---|---|---|---|---|---|
| 1 | (—)-Methyl L-lactate | 1, Ru | 1000 | 16 | MeOH | MeOK, 5 | 100 | 86 |
| 2 | Ethyl acetate | 1, Ru | 20000 | 16 | neat | EtONa, 1 | 40 | 99[b] |
| 3 | Ethyl acetate | 1, Ru | 40000 | 14 | neat | EtONa, 1 | 40 | 95[b] |
| 4 | Ethyl acetate | 1, Ru | 80000 | 21 | neat | EtONa, 1 | 40 | 73[c] |
| 5 | Ethyl benzoate | 1, Ru | 20000 | 16 | THF | EtONa, 1 | 40 | 85 |
| 6 | Methyl benzoate | 1, Ru | 4000 | 6 | THF | tBuOK, 1 | 40 | 95 |
| 7 | N-Benzylideneaniline | 1, Ru | 20000 | 1.5 | THF | tBuOK, 1 | r.t. | 100 |
| 8 | 2-methoxymethyl acetate | 1, Ru | 10000 | 16 | THF | MeOK, 1 | 60 | 100 |
| 9 | 3-methoxymethyl propionate | 1, Ru | 2000 | 21 | THF | MeOK, 2 | r.t. | 97 |
| 10 | dimethyl phthalate | 1, Ru | 2000 | 2 | THF | MeOK, 2 | 100 | 53 |
| 11 | dimethyl phthalate | 1, Ru | 2000 | 4 | THF | MeOK, 2 | 100 | 67 |
| 12 | dimethyl phthalate | 1, Ru | 2000 | 1 | THF | MeOK, 2 | 100 | 100 |
| 13 | dimethyl iso-phthalate | 1, Ru | 1000 | 1 | THF | MeOK, 2 | 100 | 100 |
| 14 | dimethyl iso-phthalate | 1, Ru | 2000 | 16 | THF | MeOK, 2 | 40 | 100 |
| 15 | Methyl benzoate | 2, Os | 2000 | 2 | THF | MeOK, 1 | 100 | 81 |
| 16 | Acetophenone | 1, Ru | 20000 | 1.42 | THF | tBuOK, 1 | r.t. | 100[d] |
| 17 | Acetophenone | 1, Ru | 40000 | 24 | THF | tBuOK, 1 | 40 | 100[d] |
| 18 | Cyclohexanone | 1, Ru | 100000 | 24 | THF | tBuOK, 1 | r.t. | 100[d] |

[a]reactions were performed using 20 mmol of the substrates in THF at 100° C. and 50 Bar of H₂ pressure in a 75 mL autoclave.
[b]reaction was performed in a 300 mL autoclave using 0.2 mol of the substrate.
[c]reaction was performed in a 300 mL autoclave using 0.4 mol of the substrate.
[d]reaction was performed in a 300 mL autoclave using 0.1 mol of the substrate and 15 mL of THF.

Example 16. Typical Procedure for Acceptorless Alcohol Dehydrogenation

In an argon glovebox, a 50 mL Schlenk tube equipped with a stirbar was charged with 0.02 mmol of the catalysts 1 or 2 and 136 mg (2.0 mmol) of EtONa. Then, 9.21 g (0.2 mol) of ethanol was added. After taking the stoppered flask out of the box, it was attached to a vacuum/Ar manifold. Under argon, the stopper was replaced by a finger condenser connected to a circulating refrigerated bath. When the temperature in the bath reached −10° C., the flask was placed in an oil bath preheated to 90° C. During dehydrogenation, the argon tank was kept closed and the H₂ gas produced passed through a mineral oil bubbler. The conversion to product was monitored by ¹H NMR spectroscopy.

Example 17. Catalytic Studies

An attractive "green" alternative to the classical methods for reduction of carboxylic esters is the catalytic hydrogenation shown in Scheme 1, a method which has attracted much recent interest for the reduction of esters under H₂. [3-7]

Scheme 1. Ester hydrogenation catalysts

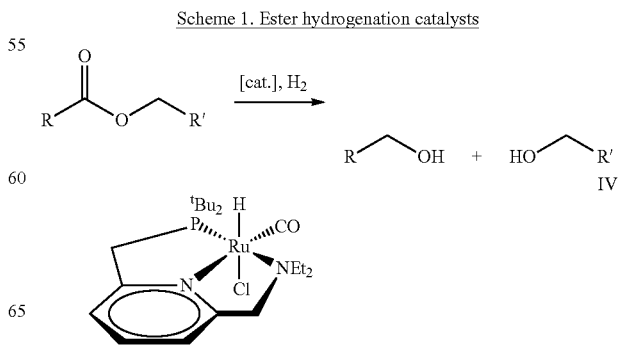

-continued

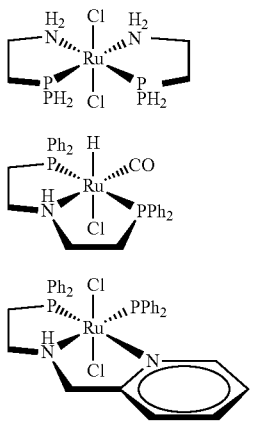

The disclosure of Milstein's catalysts in 2006 (such as complex IV; Scheme 1)[3] was quickly followed by the development of the Firmenich catalysts in 2007,[4] among which [RuCl$_2$(H$_2$NC$_2$H$_4$PPh$_2$)$_2$] (II) is effective at 100° C. at a 0.05 mol % catalyst loading.[4a] In 2011, a new catalyst, Ru-MACHO (III), was patented by Takasago chemists.[5] Ru—MACHO is useful at a 0.05 mol % loading for the hydrogenation of methyl lactate and methyl menthoxyacetate, giving high yields of (R)-1,2-propanediol and 2-(1-menthoxy) ethanol, respectively. The most recent additions to this list of efficient catalysts are osmium and ruthenium complexes from the present inventors,[6] particularly the air-stable complex [RuCl$_2$—(PPh$_3$){PyCH$_2$NHC$_2$H$_4$PPh$_2$}] (IV), which demonstrated unprecedented activity in the hydrogenation of esters and imines at [Ru] loadings as low as 50 ppm at 40° C.

It can be seen that all of the ester hydrogenation catalysts in Scheme 1 possess amino-phosphine ligands. More generally, many Noyori-type catalysts incorporate a combination of phosphorus and nitrogen donors.[8] Despite the widespread application and tremendous success of phosphines in catalysis, they have well-known disadvantages. Their preparations are often far from trivial and require handling under an inert atmosphere. As a result, the amino-phosphines are costly chemicals that can be challenging to make on a large scale. Not surprisingly, catalysts I-III (available from Strem Chemicals) are very expensive, especially I, which costs $680 per gram. Considering that ruthenium contributes less than 1% to this cost, it is apparent that the development of practical ester hydrogenation calls for using practical ligands, preferably ones containing no phosphorus.

In the present study, the catalytic activity of ruthenium complexes with the HN(C2H4SEt)2 (SNS) ligand was evaluated for ester hydrogenation. The SNS ligand was obtained nearly quantitatively by adding bis-(2-chloroethyl) amine hydrochloride to a solution of ethanethiol and NaOH in ethanol.[9b] This synthesis has the practical advantages of being straightforward and scalable; it can be conveniently performed in air, and it provides the SNS ligand at a small fraction of the cost of the amino-phosphines used in catalysts I-IV. The present application provides details of the preparation of an air-stable ruthenium-SNS complex that has now been found to be the most efficient catalyst for ester hydrogenation to date, outperforming the known catalytic systems I-III by a large margin. The significance of this finding goes beyond ester hydrogenation. It is now apparent that a new class of catalysts for the Noyori-type hydrogenation of compounds with C═X bonds can be made based on amino-sulfides that have the potential to replace the ubiquitous phosphorus-based ligands used in this area.

Figure 3:
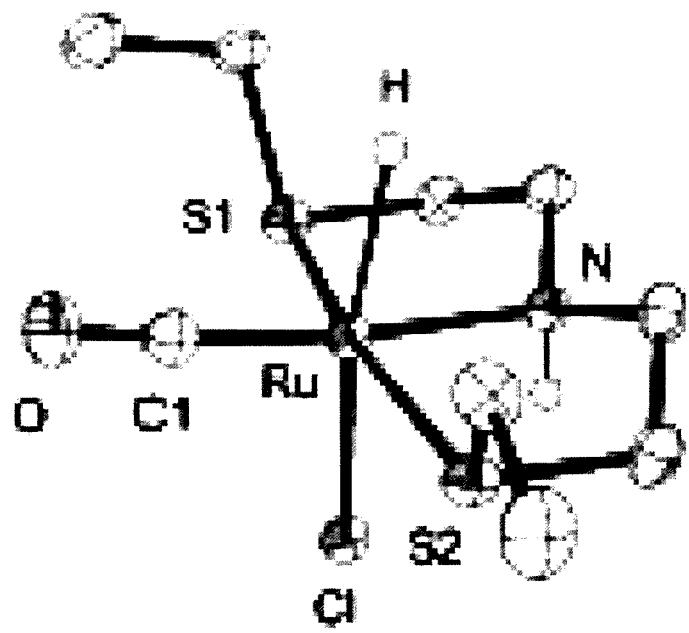
FIG. 3 is an ORTEP diagram for complex 5 (Example 9), thermal ellipsoids are at 50% probability (the hydrogen atoms are omitted for clarity)

The ruthenium complexes shown below were obtained by the conventional ligand substitution reactions of HN—(C$_2$H$_4$SEt)$_2$ with [RuCl$_2$(PPh$_3$)$_3$], [RuHCl(PPh$_3$)$_3$], [RuCl$_2$(AsPh3)3], and [RuHCl(CO)(PPh$_3$)$_3$], as documented in the above Examples. Complexes 1 and 5 have been crystallographically characterized and their molecular geometries are presented in FIGS. 1 and 3.[10]

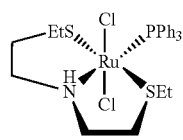

1

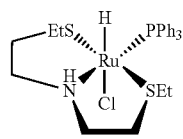

3

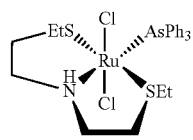

4

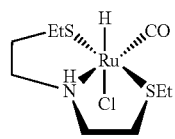

5

The catalytic results of this Example are organized in Tables 3 and 4. First, the effectiveness of catalysts III-VII and present complexes 1, 3-5 were compared. Two typical substrates were selected for the comparative study: methylbenzoate and methyl hexanoate. The hydrogenations were performed at 40° C., under H$_2$ (50 bar), using a catalyst loading of 0.05 mol % in all cases. The reaction mixtures were analyzed by $^1$H NMR spectroscopy after 3 h of hydrogenation.

TABLE 3

Comparative hydrogenation with catalysts III-VII and catalysts 1, 3-5.

| Substrate | Catalyst | | | | | | | |
|---|---|---|---|---|---|---|---|---|
| | IV | V | VI | VII | 1 | 3 | 4 | 5 |
| PhCO$_2$Me | 4 (3)[b] | 63 (6)[b] | 4 (3)[b] | 75 (6)[b] | 86 (2)[b] | 84 (3)[b] | 57 (6)[b] | 45 (7)[b] |
| C$_5$H$_{11}$CO$_2$Me | 18 (7)[c] | 55 (16)[c] | 23 (8)[c] | 89 (10)[c] | 98 (1)[c] | 96 (1)[c] | 75 (13)[c] | 66 (17)[c] |

[a] Conditions: ester (0.1 mol), catalyst (0.05 mol %), KOMe (5 mol %) in THF (15 mL) under H$_2$ (50 bar) for 3 h at 40°C.
[b]Concentration (mol %) of benzyl alcohol in the product mixture; data in parentheses is the concentration (mol %) of benzyl benzoate. The balance of material present was unreacted starting material.
[c]Concentration (mol %) of 1-hexanol in the product mixture; data in parentheses is the concentration (mol %) of hexyl hexanoate. The balance of material present was unreacted starting material.

TABLE 4

Hydrogenation of the substrates catalyzed by complex 1

| Entry | Substrate | S/C[b] | Base | Solvent | t [h] | T[° C.] | Conv. [%] |
|---|---|---|---|---|---|---|---|
| 1 | E1 | 4000 | tBuOK | THF | 6 | 40 | 95 |
| 2 | E2 | 20000 | EtONa | THF | 16 | 40 | 85[c] |
| 3 | E3 | 1000 | MeOK | THF | 1.2 | 100 | 96 |
| 4 | E4 | 2000 | MeOK | THF | 16 | 40 | 93 |
| 5 | E4 | 1000 | MeOK | THF | 1 | 100 | 100 |
| 6 | E5 | 40000 | EtONa | neat | 14 | 40 | 95[d] |
| 7 | E5 | 80000 | EtONa | neat | 21 | 40 | 73[d] |
| 8 | E6 | 20000 | MeOK | THF | 24 | 40 | 81[c,e] |
| 9 | E6 | 10000 | MeOK | THF | 2 | 100 | 98[c] |
| 10 | E7 | 10000 | MeOK | THF | 16 | 60 | 100[c] |
| 11 | E8 | 2000 | MeOK | THF | 21 | 23 | 97 |
| 12 | E9 | 4000 | tBuOK | neat | 1 | 100 | 100 |
| 13 | E10 | 2000 | tBuOK | THF | 8 | 40 | 100[f] |
| 14 | E11 | 2000 | MeOK[g] | toluene | 1 | 100 | 93 |
| 15 | E12 | 10000 | MeOK | toluene | 2 | 100 | 99 |
| 16 | I1 | 20000 | tBuOK | THF | 1.5 | 23 | 100 |
| 17 | I2 | 50000 | MeOK | THF | 1 | 40 | 63 |
| 18 | I3 | 2000 | tBuOK | toluene | 6 | 40 | 100 |
| 19 | K1 | 40000 | tBuOK | THF | 24 | 40 | 100[c,h] |
| 20 | K2 | 20000 | tBuOK | THF | 1 | 23 | 100[c,h] |
| 21 | K3 | 20000 | tBuOK | THF | 2 | 23 | 100[c,h,i] |
| 22 | K4 | 20000 | tBuOK | THF | 1 | 40 | 100[c,h] |
| 23 | A1 | 10000 | MeOK | toluene | 1.5 | 100 | 94 |
| 24 | O1 | 2000 | tBuOK | THF | 20 | 40 | 100 |
| 25 | O2 | 2000 | MeOK | THF | 48 | 40 | 75 |
| 26 | O3 | 2000 | MeOK | THF | 48 | 40 | 13 |

[a] Unless otherwise noted, the reaction was carried out on substrate (0.02 mol) with base additive (1 mol %) in solvent (6 mL) in a 75 mL Parr high-pressure vessel.
[b]Substrate to catalyst ratio.
[c]Substrate (0.1 mol) was hydrogenated in a 0.3 L vessel.
[d]Substrate (0.2 mol) was hydrogenated in a 0.3 L vessel.
[e]The product also contained hexyl hexanoate (9%).
[f]Trans-3-nonen-1-ol/1-nonanol = 73:27.
[g]5 mol % of base was used.
[h]in 15 mL of THF.
[i]Cis/trans product ratio = 87:13.

In all cases, they were found to contain the product alcohols together with varied amounts of byproduct from transesterification, as well as methanol and unreacted starting material. The results in Table 3 demonstrate that the Milstein and Takasago catalysts IV and V are the least effective in the group and produce little product under the test conditions. The Firmenich catalyst V shows a moderate performance, whereas complex VII is the most effective of the known systems. The new catalysts 1 and 3-5 are all active for esterhydrogenation; among these, the dichloride and hydrido-chloride complexes 1 and 3 give the best conversions to products, accompanied by formation of the smallest amounts of the symmetrical ester byproducts. To gain a broader understanding of the catalytic performance of complex 1, it was tested in the hydrogenation of the diverse group of substrates shown below, accompanied by variation of the reaction temperature, time, and substrate-to-catalyst (S/C) ratios.

Esters

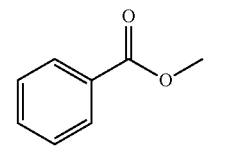

E1

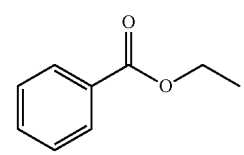

E2

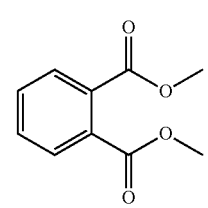

E3

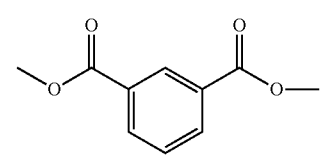

E4

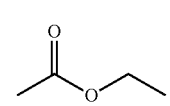

E5

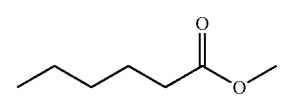

E6

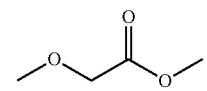

E7

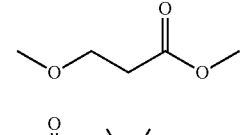

E8

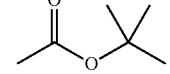

E9

-continued

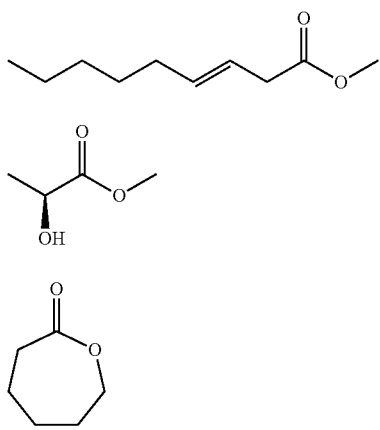

Imines

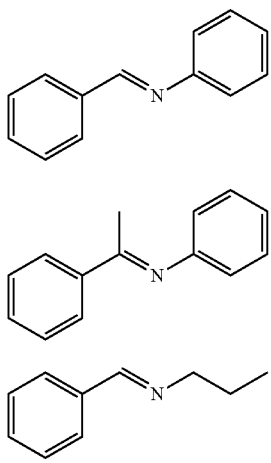

Ketones and Aldehydes

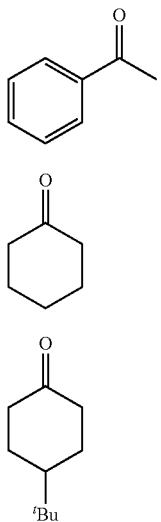

-continued

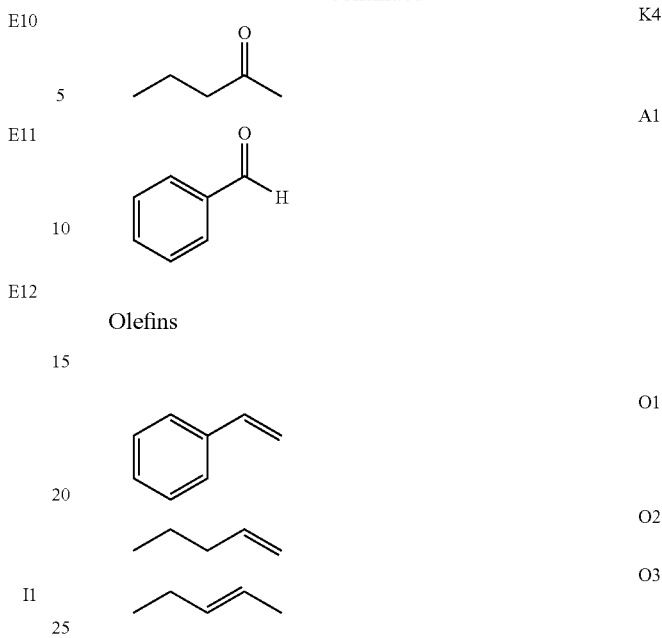

Olefins

The data in Table 4 support the assessment of complex 1 as an outstanding hydrogenation catalyst possessing excellent efficiency and thermal stability and longevity in catalytic solutions. Large turnover numbers were observed for methyl and ethyl benzoates E1 and E2, respectively. For methyl hexanoate (E6), a high TON of 9800 is achieved in 2 h at 100° C. with 1, whereas Firmenich catalyst IV is known to be 6.5 times slower at this temperature for a similar substrate, methyl octanoate, giving a TON of 1880 after 2.5 h.[4a] The reduction of neat ethyl acetate (E5) is particularly impressive with 1, affording a TON of 58 400 after 21 h under very mild reaction conditions (T=40° C.). A relatively difficult substrate, methyl phthalate (E3) is also rapidly reduced with 1 (0.1 mol %) at 100° C.

Catalyst 1 was successfully tested for the hydrogenation of typical imines and ketones shown above, where TONs up to 40000 have been observed when running the reactions at 23-40° C. Catalyst 1 also has some activity for olefin hydrogenation. Styrene was reduced relatively rapidly at 40° C. with 1 (0.05 mol %). However, the reduction of 1-pentene was considerably slower, and 2-pentene was largely unchanged even after 48 h at 40° C. The latter observation is promising for the selective hydrogenation of esters, ketones, and imines containing internal C=C bonds. For example, the hydrogenation of methyl 3-nonenoate at 40° C. afforded trans-3-nonen-1-ol in a 73% yield. Such selectivity is rare among catalysts that are active for ester hydrogenation. So far, only one ruthenium catalyst from Firmenich[4] and an osmium catalyst from our group[6a] have shown good selectivity for the reduction of esters with internal C=C bonds.

As commented recently,[6b] high catalytic efficiency in ester hydrogenation is expected to correlate with activity in the reverse reaction of acceptorless dehydrogenative coupling (ADC) of alcohols, affording symmetrical esters. Indeed, when tested in the ADC reaction of ethanol under reflux, with S/C=2000 and 10 000, complex 1 gave 97% and 89% conversion to ethyl acetate in 16 and 24 h, respectively. This performance is similar to that of catalyst VII, and complexes 1 and VII are currently among the most efficient ADC catalysts.[11]

Figure 4:
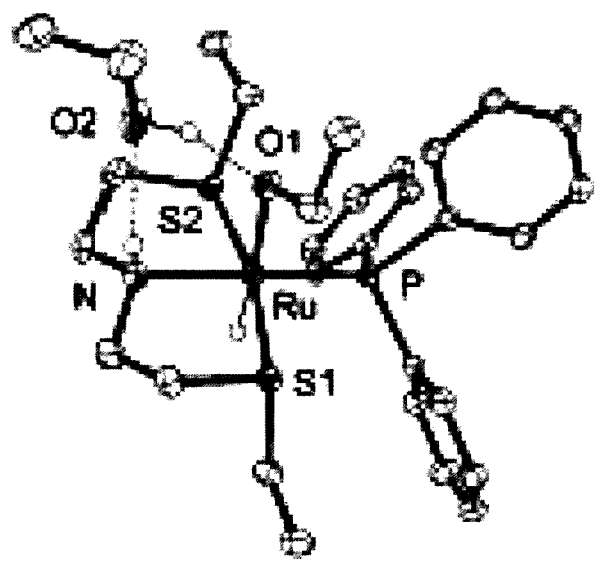
FIG. 4 is an ORTEP diagram for complex 6-EtOH (Example 10), thermal ellipsoids are at 50% probability (the hydrogen atoms are omitted for clarity)
Figure 5:
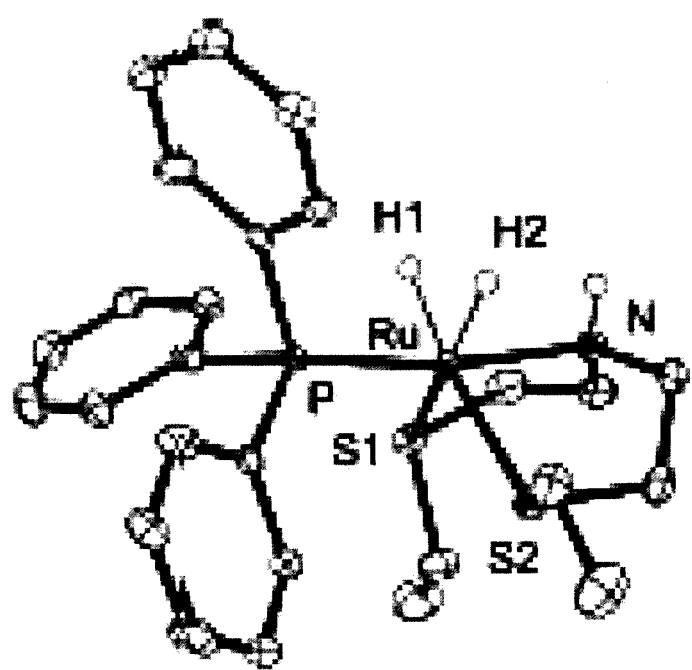
FIG. 5 is an ORTEP diagram for complex 7 (Example 11), thermal ellipsoids are at 50% probability (the hydrogen atoms are omitted for clarity).

When studying the reactions of complex 1 upon heating in basic ethanol, a quantitative conversion of the dichloride into species 6 was observed, which was isolated and characterized as [RuH(OEt)(PPh$_3$){HN(C$_2$H$_4$SEt)$_2$}] and crystallized with one equivalent of hydrogen-bonded ethanol, 6.EtOH (FIG. 4). The preparation of 6 containing no ethanol was also possible by treating hydrido-chloride species 3 with EtONa in toluene. Interestingly, whereas 6 is thermally stable in solution, 6.EtOH is readily and selectively converted into [RuH$_2$(PPh$_3$){HN(C$_2$H$_4$SEt)$_2$}] (7) and ethyl acetate upon mild heating in toluene, as shown in Scheme 2.[12] The molecular structure of 7 is presented in FIG. 5; unlike the related mer-SNS compounds 1-6, the dihydride 7 adopts a fac-SNS geometry.

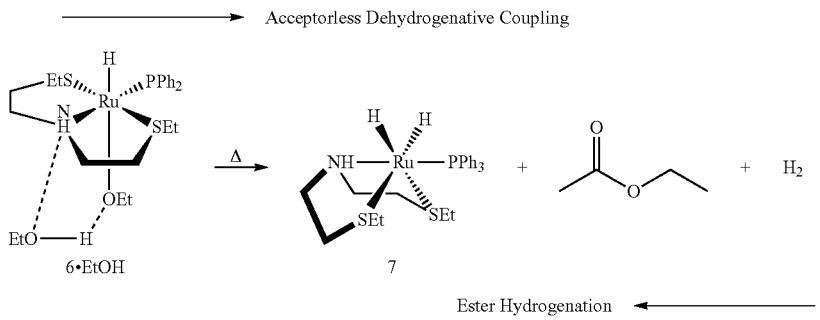

Scheme 2. Formation of dihydride 7 from 6-EtOH

Scheme 2 has mechanistic implications, as the forward reaction is part of the ADC process, whereas the reverse reaction is ester hydrogenation. Complex 6.EtOH rapidly hydrogenates ethyl acetate at room temperature (23° C.), giving 77% conversion into ethanol within 1 h, under H$_2$ (50 bar), with [Ru] (0.02 mol %) and NaOEt (1 mol %) and with an efficiency corresponding to TOF=3850 h$^{-1}$. Without wishing to be bound by theory, it appears that dihydride 6 is the hydrogenation catalyst involved in this process, as well as in the reactions of Table 4, where 6 is presumably produced under H$_2$ from 1 and base. The NH group also appears to be important for catalysis. We synthesized two analogues of catalyst 1: [RuCl$_2$(PPh$_3$){O(C$_2$H$_4$SEt)$_2$}] (8) and [RuCl$_2$(PPh$_3$){MeN(C$_2$H$_4$SEt)$_2$}] (9), and these complexes proved to be inactive in the hydrogenation of methyl benzoate at 40-100° C., under the reaction conditions given in Table 3.

The mechanism of ester hydrogenation is poorly understood.[7i] According to Milstein et al[3a] and Saudan et al,[4a] the concerted transfer of a metal hydride and a ligand proton to the C=O group of the substrate first takes place, affording a hemiacetal intermediate. Dissociation of the hemiacetal gives rise to an aldehyde, which is hydrogenated again by the catalyst, thus completing the reduction process. In the present study, examination of the reaction mixtures by 1H NMR spectroscopy gave no evidence of the presumed hemiacetal oraldehyde intermediates of ester hydrogenation, ethanoldehydrogenation reactions, or the reaction shown in Scheme 2. It is likely that no free organic intermediate, hemiacetal or aldehyde, is released into the reaction solution during the reactions catalyzed by the SNS complexes presented herein.

A tentative mechanism for the base-free hydrogenation of ethyl acetate catalyzed by 6 is presented in Scheme 3. Free energies for all of the intermediates shown in Scheme 3 were calculated in ethyl acetate using the M06-L functional.

Among the proposed key steps is the insertion of ethylacetate into a Ru—H bond of 7, to afford Int 1, which is analogous to the hemiacetaloxide formation in the reaction of trans-[RuH$_2${(R)-BINAP}{(R,R)-dpen}] with g-butyrolactone, as documented by Bergens et al.[7g] Inspection of the DFT-optimized structure of Int 1 revealed an interesting feature:Int 1 has a six-membered cycle formed by the H—N—Ru—OCH(Me)-OEt groups and closed by an NH—O hydrogen bond (d$_{O-H}$=1.92 Å). The single C—O bond of Int 1 is elongated to 1.493 Å from the corresponding 1.345 Å distance in ethylacetate. Without wishing to be bound by theory, it is conceivable that intramolecular nucleophilic substitution in step b results in the formation of bis(ethoxide) Int 2, which rearranges in step c to afford the dihydrogen complex Int 3. Heterolytic splitting of the η$^2$-H$_2$ ligand in step d gives Int 4. Ethanol elimination accompanied by H$_2$ coordination and heterolysis in steps e and f regenerate dihydride 7. The isolated complex 6.EtOH (a mer-SNS isomer of Int 4) is apparently a resting state of the catalyst. Formation of 6 EtOH from 7, ethyl acetate, and H$_2$ is favorable by ΔG=−6.2 kcalmol$^{-1}$, which is 6.7 kcalmol$^{-1}$ more stable than Int 4.

Scheme 3. Base-free reduction of ethyl acetate catalyzed by complex 7

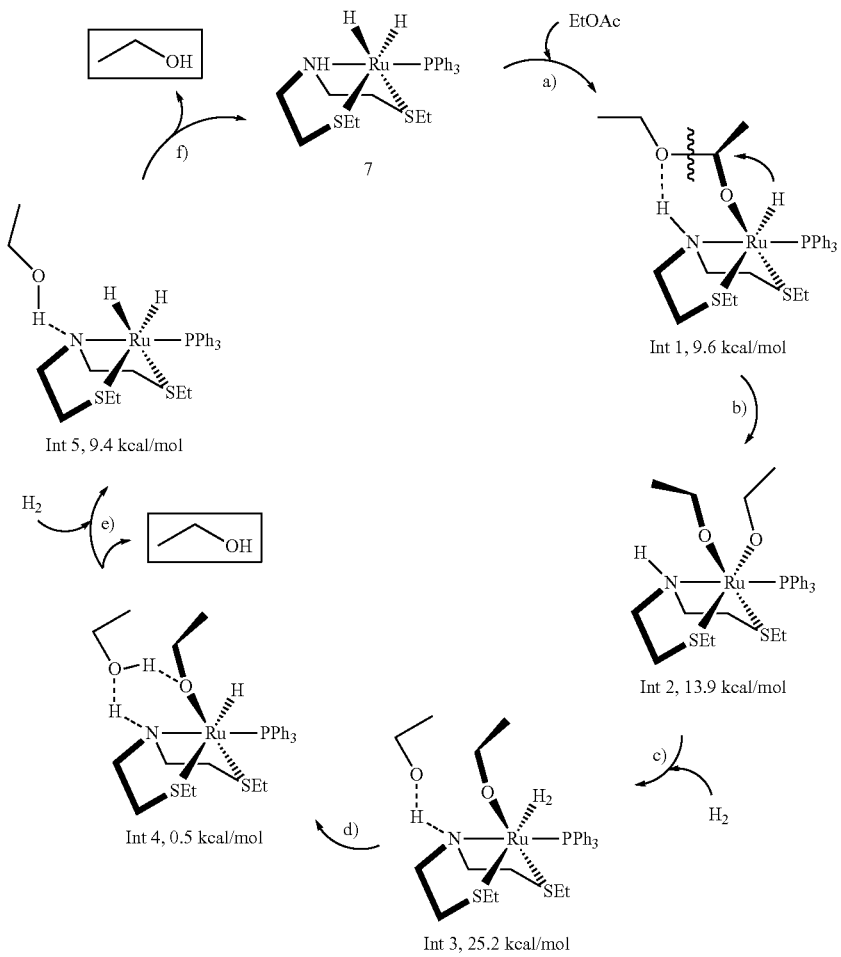

Base has a tremendous accelerating effect on the hydrogenation rate. Without base, 6.EtOH (0.02 mol %) gave only 4% conversion into ethyl acetate in 2 h at 40° C. under $H_2$ (50 bar), which corresponds to TOF=$100^{-1}$ vs. TOF=4100 $h^{-1}$ with NaOEt (1 mol %) in 1 h under otherwise identical conditions. According to Bergens et al,[13] base helps by labilizing the alkoxide intermediates (such as Int 2 and Int 4) for EtO$^-$ substitution, through deprotonation of the NH group.

In conclusion, this Example demonstrates the successful use of embodiments of the present catalysts based on the HN($C_2H_4$SEt)$_2$ ligand. The air-stable complex [RuCl$_2$(PPh$_3$)]{HN—($C_2H_4$SEt)$_2$}] (1) shows outstanding efficiency for the hydrogenation of a broad range of substrates with C=X bonds (esters, ketones, imines) as well as for the acceptor-less dehydrogenative coupling of ethanol to ethyl acetate. This study has demonstrated that the phosphorus groups of Noyori-type catalysts can be successfully replaced by sulfide groups, thus overcoming the many drawbacks of working with phosphines and phosphine-based catalysts, such as high synthetic costs and the need for handling under inert atmosphere. Complex 1 is a practical and highly active green hydrogenation catalyst for substrates with C=X (X=O, N) bonds, and has a high potential to replace the use of main-group hydrides for the reduction of esters in the chemical industry and academic laboratories.

REFERENCES

[1] a) Comprehensive Organic Synthesis, Vol. 8 (Eds.: B. M. Trost, I. Fleming), Pergamon, New York, 1991; b) J. Seyden-Penne, Reductions by the Alumino- and Borohydride in Organic Synthesis, 2nd ed., Wiley-VCH, New York, 1997.
[2] P. Vogt, B. Bodnar, Spec. Chem. Mag. 2009, 29/7, 22-24.
[3] a) J. Zhang, G. Leitus, Y. Ben-David, D. Milstein, Angew. Chem. 2006, 118, 1131-1133; Angew. Chem. Int. Ed. 2006, 45, 1113-1115; b) E. Balaraman, C. Gunanathan, J. Zhang, L. J. W. Shimon, D. Milstein, Nat. Chem. 2011, 3, 609-614; c) E. Fogler, E. Balaraman, Y. Ben-David, G. Leitus, L. J. W. Shimon, D. Milstein, Organometallics 2011, 30, 3826-3833; d) C. Gunanathan, D. Milstein, Acc. Chem. Res. 2011, 44, 588-602; e) D. Milstein, E. Balaraman, C. Gunanathan, B. Gnanaprakasam, J. Zhang, WO 2012/052996A2, 2012.
[4] a) L. A. Saudan, C. M. Saudan, C. Debieux, P. Wyss, Angew. Chem. 2007, 119, 7617-7620; Angew. Chem. Int. Ed. 2007, 46, 7473-7476; b) L. Saudan, P. Dupau, J.-J. Riedhauser, P. Wyss (Firmenich SA), WO 2006106483, 2006; c) L. Saudan, P. Dupau, J.-J. Riedhauser, P. Wyss (Firmenich SA), US 2010280273, 2010.
[5] a) W. Kuriyama, Y. Ino, O. Ogata, N. Sayo, T. Saitoa, Adv. Synth. Catal. 2010, 352, 92-96; b) Y. Ino, W.

Kuriyama, O. Ogata, T. Matsumoto, Top. Catal. 2010, 53, 1019-1024; c) W. Kuriyama, T. Matsumoto, Y. Ino, O. Ogata, N. Saeki (Takasago Int. Co.), WO2011048727, 2011.

[6] a) D. Spasyuk, S. Smith, D. G. Gusev, Angew. Chem. 2012, 124, 2826-2829; Angew. Chem. Int. Ed. 2012, 51, 2772-2775; b) D. Spasyuk, D. G. Gusev, Organometallics 2012, 31, 5239-5242.

[7] a) Y. Sun, C. Koehler, R. Tan, V. T. Annibale, D. Song, Chem. Commun. 2011, 47, 8349-8351; b) F. Stempfle, D. Quinzler, I. Heckler, S. Mecking, Macromolecules 2011, 44, 4159-4166; c) M. J. Hanton, S. Tin, B. J. Boardman, P. Miller, J. Mol. Catal. A2011, 346, 70-78; d) W. W. N. O, A. J. Lough, R. H. Morris, Chem. Commun. 2010, 46, 8240-8242; e) T. Touge, T. Hakamata, H. Nara, T. Kobayashi, N. Sayo, T. Saito, Y. Kayaki, T. Ikariya, J. Am. Chem. Soc. 2011, 133, 14960-14963; f) M. Ito, T. Ootsuka, R. Watari, A. Shiibashi, A. Himizu, T. Ikariya, J. Am. Chem. Soc. 2011, 133, 4240-4242; g) S. Takebayashi, S. H. Bergens, Organometallics 2009, 28, 2349-2351; h) I. Carpenter, S. C. Eckelmann, M. T. Kuntz, J. A. Fuentes, M. B. France, M. L. Clarke, Dalton Trans. 2012, 41, 10136-10140; i) M. L. Clarke, Catal. Sci. Technol. 2012, 2, 2418-2423; j) W. W. N. O, R. H. Morris, ACS Catal. 2013, 3, 32-40.

[8] For recent reviews, see: a) C. Wang, X. F. Wu, J. L. Xiao, Chem. Asian J. 2008, 3, 1750-1770; b) S. Gladiali, E. Alberico, Chem. Soc. Rev. 2006, 35, 226-236; c) J. S. M. Samec, J. E. Backvall, P. G. Andersson, P. Brandt, Chem. Soc. Rev. 2006, 35, 237-248; d) T. Ikariya, K. Murata, R. Noyori, Org. Biomol. Chem. 2006, 4, 393-406; e) S. E. Clapham, A. Hadzovic, R. H. Morris, Coord. Chem. Rev. 2004, 248, 2201-2237; f) R. Noyori, Angew. Chem. 2002, 114, 2108-2123; Angew. Chem. Int. Ed. 2002, 41, 2008-2022.

[9] a) D. S. McGuinness, P. Wasserscheid, D. H. Morgan, J. T. Dixon, Organometallics 2005, 24, 552-556; b) M. Konrad, F. Meyer, K. Heinze, L. Zsolnai, J. Chem. Soc. Dalton Trans. 1998, 199-205.

[10] The mer-SNS complexes form isomers in solution. This is due to the different arrangements of the SEt groups relative to the SNS ligand plane. Two of the isomers have eclipsed SEt groups (arranged on one side of the SNS plane), and the third isomer has staggered SEt groups (occupying the opposite sides of the SNS plane).

[11] a) J. Zhang, G. Leitus, Y. Ben-David, D. Milstein, J. Am. Chem. Soc. 2005, 127, 10840-10841; b) J. Zhang, M. Gandelman, L. J. W. Shimon, D. Milstein, Dalton Trans. 2007, 107-113; c) J. Zhang, E. Balaraman, G. Leitus, D. Milstein, Organometallics 2011, 30, 5716-5724; d) C. Gunanathan, L. J. W. Shimon, D. Milstein, J. Am. Chem. Soc. 2009, 131, 3146-3147; e) C. del Pozo, M. Iglesias, F. S_nchez, Organometallics 2011, 30, 2180-2188; f) S. Musa, I. Shaposhnikov, S. Cohen, D. Gelman, Angew. Chem. 2011, 123, 3595-3599; Angew. Chem. Int. Ed. 2011, 50, 3533-3537; g) M. Nielsen, A. Kammer, D. Cozzula, H. Junge, S. Gladiali, M. Beller, Angew. Chem. 2011, 123, 9767-9771; Angew. Chem. Int. Ed. 2011, 50, 9593-9597; h) M. Nielsen, H. Junge, A. Kammer, M. Beller, Angew. Chem. 2012, 124, 5809-5811; Angew. Chem. Int. Ed. 2012, 51, 5711-5713.

[12] A related transformation of a ruthenium isopropoxide into a hydride species, facilitated by isopropanol, has been studied; see: W. Baratta, M. Ballico, G. Esposito, P. Rigo, Chem. Eur. J. 2008, 14, 5588-5595.

[13] R. J. Hamilton, S. H. Bergens, J. Am. Chem. Soc. 2006, 128, 13700-13701; see also Ref. [7g].

Experimental

In all cases, the catalytic reactions were studied by $^1$H NMR spectroscopy using approximately 0.65 mL samples taken from the reactions mixtures without dilution or mixing with other solvents. The NMR spectra were collected without 2H lock, using 0.3 µs 1H pulses and a 10 s acquisition time to ensure accurate integration of the peaks. Examples of typical dehydrogenation and hydrogenation procedures are given below.

Hydrogenation Using Complex 1.

In an argon glovebox, the required amount of a 1.9 mg/g solution of 1 in THF was added to the desired amount of base (tBuOK, MeOK, or EtOK). The catalyst solution was further mixed with the substrate (0.02-0.20 mol) and transferred into a stainless-steel Parr reactor (75 mL or 300 mL) equipped with a magnetic stir bar. The reactor was closed, taken out of the glovebox, tightened and connected to a hydrogen tank. After purging the line, the reactor was pressurized to $p(H_2)$=725 psi (50 Bar) and disconnected from the $H_2$ source (with the exception of reactions conducted in the 300 mL reactor using 0.2 mol of substrate). Then, the reactor was placed in an oil bath preheated to the desired temperature. At the end of the reaction time, the reactor was moved into a cold water bath for 5 min and depressurized.

Ethanol Dehydrogenation.

In an argon glovebox, a 50 mL Schlenk tube equipped with a stir bar was charged with the required amounts of the catalyst and EtONa. Then, 4.61 g (0.1 mol) or 9.21 g (0.2 mol) of ethanol was added. After taking the stoppered flask out of the box, it was attached to a vacuum/Ar manifold. Under argon, the stopper was replaced by a finger condenser connected to a circulating refrigerated bath. When the temperature in the bath reached −10° C., the flask was placed in an oil bath preheated to 90° C. During dehydrogenation, the argon tank was kept closed and the $H_2$ gas produced passed through a mineral oil bubbler.

Crystal Structure Determination.

Single crystals of complexes 1 and 5 were grown by slow diffusion of hexanes into their saturated solutions in dichloromethane. Single crystals of complexes 6 and 7 were grown by slow diffusion of hexanes into their saturated solutions in toluene. The crystallographic data for complexes 1, 5, 6, and 7 were collected on a BrukerAPEX II QUAZAR equipped with the IµS™ X-ray Source generator, a Kappa Nonius goniometer and a Platinum 135 detector. Cell refinement and data reduction were done using SAINT. [SAINT (1999) Release 6.06; Integration Software for Single Crystal Data. Bruker AXS Inc., Madison, Wis., USA] An empirical absorption correction, based on the multiple measurements of equivalent reflections, was applied using the program SADABS. [Sheldrick, G. M. (1999). SADABS, Bruker Area Detector Absorption Corrections. Bruker AXS Inc., Madison, Wis., USA] The space group was confirmed by XPREP routine [XPREP (1997) Release 5.10; X-ray data Preparation and Reciprocal space Exploration Program. Bruker AXS Inc., Madison, Wis., USA] of SHELXTL. [SHELXTL (1997) Release 5.10; The Complete Software Package for Single Crystal Structure Determination. Bruker AXS Inc., Madison, Wis., USA] The structures were solved by direct-methods and refined by full-matrix least squares and difference Fourier techniques with SHELX-97 [(a) Sheldrick, G. M. (1997). SHELXS97, Program for the Solution of Crystal Structures. Univ. of Gottingen, Germany. (b) Sheldrick, G. M. (1997). SHELXL97, Program for the Refinement of Crystal Structures. University of Gottingen, Germany.] as a part of LinXTL [LinXTL is a local program and it can be obtained free of charge from http://sourceforge.net/projects/linxtl/] tool box. All non-hydrogen atoms were refined with anisotropic displacement parameters. Hydrogen atoms were set in calculated positions and refined as riding atoms with a common thermal parameter, except those of the NH, OH moieties and hydrides, which were positioned from residual peaks in the difference Fourier map. All publication materials (cif files validation and ORTEP drawings) were prepared using LinXTL and Platon [A. L. Spek, *Acta Cryst.* 2009, D65, 148-155] programs.

Computational Details.

All calculations were carried out in Gaussian 09 [Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, and D. J. Fox, Gaussian, Inc., Wallingford Conn., 2009.] (revision C.01) using the M06-L functional, [Y. Zhao, D. G. Truhlar, *J. Chem. Phys.* 2006, 125, 194101-194118] tight optimizations, and the ultrafine integration grid (a pruned 99,590 grid). The basis sets, listed by their corresponding Gaussian 09 keywords, included QZVP [This basis set is also known as def2-QZVP; F. Weigend, R. Ahlrichs, *Phys. Chem. Chem. Phys.* 2005, 7, 3297.] (with the corresponding ECP [The ECPs are available from the EMSL Basis Set Library (bse.pnl.gov)]) for Ru, and TZVP [A. Schaefer, C. Huber, R. Ahlrichs, *J. Chem. Phys.* 1994, 100, 5829-5835; This basis set is also known as def-TZVP (singly polarized).] for all other atoms. The following density fitting basis sets were employed: QZVP (Ru) and TZVP fit (all other atoms). The polarizable continuum model using the integral equation formalism (IEFPCM) was used for all calculations, with the radii and non-electrostatic terms of Truhlar and co-workers' SMD solvation model (scrf=smd). [A. V. Marenich, C. J. Cramer, D. G. Truhlar, *J. Phys. Chem. B,* 2009, 113, 6378-6396] The optimized geometries were verified to have no negative frequencies by frequency calculations, which also provided the enthalpies and free energies reported here. The free energies were calculated at 298.15 K under P=249 atm (for ethyl acetate), following the approach of Martin and co-workers. [R. L. Martin, P. J. Hay, L. R. Pratt, *J. Phys. Chem. A* 1998, 102, 3565; N. Sieffert, M. Bühl, *Inorg. Chem.* 2009, 48, 4622].

TABLE 5

Crystal Data Collection and Refinement Parameters for Complexes 1, 5, 6 and 7

|  | 1 | 5 | 6 | 7 |
|---|---|---|---|---|
| crystal colour | Yellow | Green | Yellow | Yellow |
| Fw; F(000) | 627.60; 644 | 358.90; 364 | 646.82; 2704 | 558.72; 1160 |
| T (K) | 100 | 100 | 100 | 100 |
| wavelength (Å) | 1.54178 | 1.54178 | 1.54178 | 1.54178 |
| space group | P-1 | P-1 | Pbca | P2$_1$/n |
| a (Å) | 10.3422(3) | 7.3771(9) | 14.7252(3) | 11.9869(3) |
| b (Å) | 12.6042(3) | 7.4984(9) | 16.9510(4) | 14.3757(5) |
| c (Å) | 12.6473(3) | 13.496(2) | 24.6666(6) | 15.6824(6) |
| α (deg) | 95.192(1) | 84.129(2) | 90.00 | 90.00 |
| β (deg) | 110.203(1) | 76.845(2) | 90.00 | 94.104(1) |
| γ (deg) | 104.025(1) | 78.171(2) | 90.00 | 90.00 |
| Z | 2 | 2.00 | 8.00 | 4.00 |
| V (Å$^3$) | 1473.36(7) | 710.3(2) | 6157.0(2) | 2695.5(2) |
| ρ$_{calcd}$ (g-cm$^{-3}$) | 1.415 | 1.678 | 1.396 | 1.377 |
| μ (mm$^{-1}$) | 7.918 | 13.227 | 6.084 | 6.805 |
| θ range (deg); completeness | 3.68-69.92; 0.969 | 3.37-71.36; 0.968 | 3.58-71.09; 0.998 | 4.18-71.31; 0.988 |
| collected reflections; R$_\sigma$ | 23607; 0.0277 | 28192; 0.0165 | 115527; 0.0190 | 30975; 0.0248 |
| unique reflections; R$_{int}$ | 23607; 0.0318 | 28192; 0.0365 | 115527; 0.0562 | 30975; 0.0390 |
| R1$^a$; wR2$^b$ [I > 2σ(I)] | 0.0301; 0.0855 | 0.0276; 0.0724 | 0.0261; 0.0688 | 0.0291; 0.0749 |
| R1; wR2 [all data] | 0.0305; 0.0861 | 0.0284; 0.0729 | 0.0304; 0.0735 | 0.0294; 0.0752 |
| GOF | 1.040 | 1.069 | 0.991 | 1.039 |
| largest diff peak and hole | 0.728 and −1.002 | 1.184 and −0.645 | 0.695 and −0.426 | 2.708 and −0.420 |

$^a$R$_1$ = Σ(||F$_o$| − |F$_c$||)/Σ|F$_o$| $^b$wR$_2$ = {Σ[w(F$_o^2$ − F$_c^2$)$^2$]/Σ[w(F$_o^2$)$^2$]}$^{1/2}$

TABLE 6

| Calculated Energies | | | |
|---|---|---|---|
| m06-L data in ethyl acetate | E | H | G |
| H$_2$ | −1.17132046 | −1.158159 | −1.167747 |
| EtOH | −155.07589937 | −154.990661 | −155.016048 |

TABLE 6-continued

| Calculated Energies | | | |
|---|---|---|---|
| m06-L data in ethyl acetate | E | H | G |
| Etyl acetate | −307.78104471 | −307.654699 | −307.688922 |
| cis,fac-RuH$_2$(PPh$_3$)[HN(C$_2$H$_4$SEt)$_2$] | −2300.19167863 | −2299.598012 | −2299.691862 |
| Intermediate 1 | −2607.97820846 | −2607.253670 | −2607.365439 |
| Intermediate 2 | −2607.97385362 | −2607.247311 | −2607.358652 |
| Intermediate 3 | −2609.13814119 | −2608.394529 | −2608.508354 |
| Intermediate 4 | −2609.18231406 | −2608.434144 | −2608.547800 |
| trans,mer-RuH(OEt)(PPh$_3$)[HN(C$_2$H$_4$SEt)$_2$] with a hydrogen-bonded molecule of EtOH | −2609.18805999 | −2608.441394 | −2608.558406 |
| Intermediate 5 | −2455.25398381 | −2454.577389 | −2454.685224 |

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A metal complex of Formula II and III $$M(SN)_p Z_a \qquad \text{II}$$

$$M(SNS)Z_a \qquad \text{III}$$

wherein:

each Z is simultaneously or independently a hydrogen or halogen atom, a $C_1$-$C_6$ alkyl, a carbene group, a hydroxyl group, or a $C_1$-$C_7$ alkoxy radical, a nitrosyl (NO) group, CO, CNR (R=Alkyl, Aryl), nitrile, phosphite, phosphinite, or phosphine;

M is a group 7, group 8, or group 9 transition metal;

p is equal to 1 or 2, whereas a is equal to 1, 2, or 3;

SN is a bidentate coordinated ligand of Formula IA, wherein the coordinating groups of the SN ligand consist of one thio group and one nitrogen group;

SNS is a tridentate coordinated ligand of Formula IB, wherein the coordinating groups of the SNS ligand consist of two thio groups and one nitrogen group:

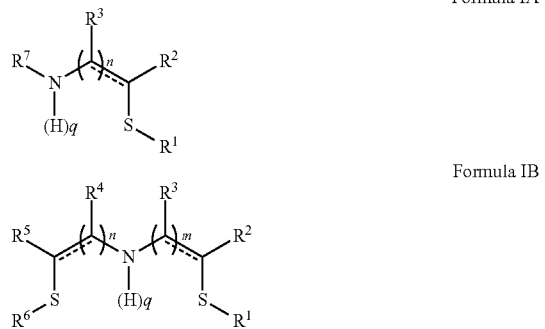

Formula IA

Formula IB where the dotted lines simultaneously or independently indicate single or double bonds;

$R^1$, $R^2$, $R^5$, and $R^6$ are each independently H, a substituted or unsubstituted linear or branched $C_1$-$C_{20}$ alkyl, a substituted or unsubstituted cyclic $C_3$-$C_8$ alkyl, or a substituted or unsubstituted $C_2$-$C_{20}$ alkenyl, a substituted or unsubstituted $C_5$-$C_{20}$ aryl, OR or $NR_2$; or when taken together, $R^1$ and $R^2$ groups or $R^5$ and $R^6$ groups can form a saturated or partially saturated $C_5$-$C_{20}$ cycle;

$R^3$ and $R^4$ are each independently H, a substituted or unsubstituted linear, branched or cyclic $C_1$-$C_8$ alkyl or alkenyl, a substituted or unsubstituted $C_5$-$C_8$ aromatic group, ester group; or, when taken together, $R^3$ and $R^4$ can form an optionally substituted saturated or partially saturated $C_5$-$C_{20}$ hetero-aromatic ring;

$R^5$ when taken together with $R^4$ can form an optionally substituted saturated or partially saturated $C_5$-$C_{20}$ aromatic ring;

$R^7$ is H, a substituted or unsubstituted linear or branched $C_1$-$C_8$ alkyl, a substituted or unsubstituted cyclic $C_3$-$C_8$ alkyl, a substituted or unsubstituted $C_2$-$C_{20}$ alkenyl, or a substituted or unsubstituted $C_5$-$C_{20}$ aryl; and n, m, and q are simultaneously or independently 0, 1, or 2.

2. A process for dehydrogenation of a substrate comprising:

treating the substrate with a catalytic amount of a metal complex of claim 1.

3. The process of claim 2, wherein the substrate comprises at least one alcohol moiety or wherein the substrate is a compound of the following Formula:

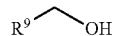

where $R^9$ is a substituted or unsubstituted alkyl or a substituted or unsubstituted aryl, wherein $R^9$ optionally comprises an amino group that undergoes dehydrogenation.

4. The process of claim 3, wherein the substrate comprises more than one hydroxyl moiety that undergoes dehydrogenation.

5. The process of claim 2, wherein the substrate and product pair of the dehydrogenation reaction is selected from the group consisting of:

| Substrate | Product |
|---|---|
| Alcohols | Ester |
| Alcohol | Aldehyde |
| Alcohol | Ketone |
| Diol | Lactone |

| Substrate | Product |
| --- | --- |
| amine + alcohol | Amide |
| amine + alcohol | substituted amine |
| amine + alcohol | Imine |
| ammonia-borane | aminoboranes |
| ammonia-borane | Borazine |
| Amine | Imine |
| Amines | Guanidine |
| alcohol + thiol | Thioester |
| Thiol alcohol + phosphine | sulphoxide acyl phosphine. |

6. A process for producing $H_2$ comprising dehydrogenation of a substrate by treating the substrate with a catalytic amount of a metal complex of claim 1.

7. The process of claim 6, wherein the substrate comprises an alcohol, amine or thiol or wherein the substrate is ammonia-borane.

8. The process of claim 2, wherein the process does not require a hydrogen acceptor.

9. The process of claim 2, which is a homogeneous process.

10. A process for hydrogenation of a substrate comprising:
treating the substrate under a pressure of hydrogen with a catalytic amount of a metal complex of claim 1.

11. The process of claim 10, wherein the substrate comprises at least one ester group.

12. The process of claim 11, wherein the process proceeds according to the following scheme

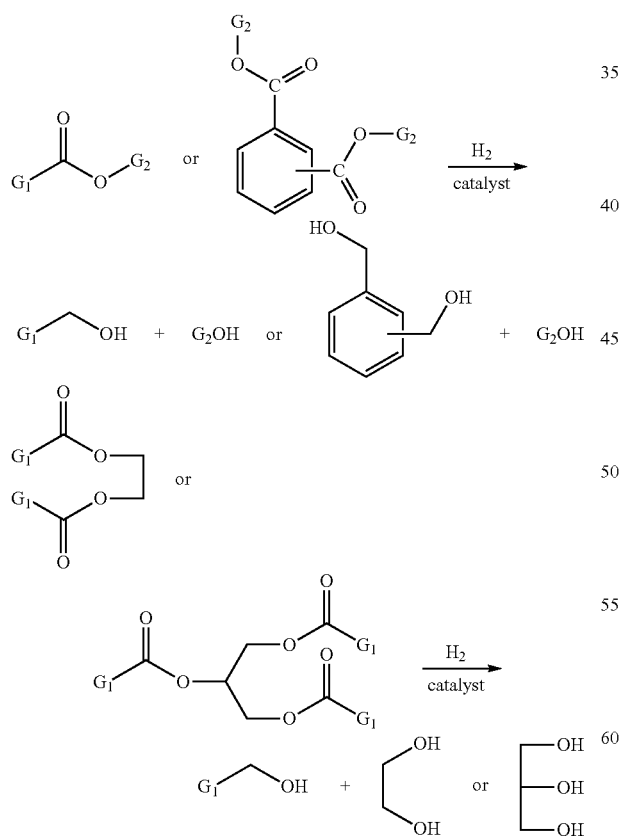

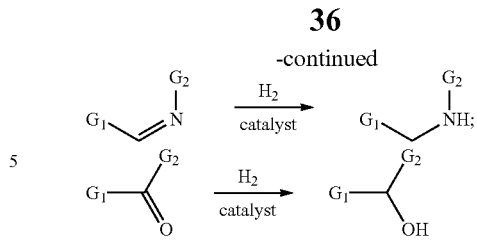

wherein $G_1$ and $G_2$, simultaneously or independently, represent a linear, branched $C_1$-$C_{40}$ or cyclic $C_3$-$C_{40}$ alkyl, alkenyl or aromatic group, optionally substituted; or $G_1$ and $G_2$ together form a $C_4$-$C_{40}$ saturated or unsaturated radical.

13. The process of claim 10, wherein the substrate and product pair of the hydrogenation reaction is selected from the group consisting of:

| Hydrogenation Substrate | Product |
| --- | --- |
| Aldehyde | alcohol |
| Ketone | alcohol |
| Ester | alcohol |
| carboxylic acid | alcohol |
| Ketene | alcohol |
| Enol | alcohol |
| Epoxide | alcohol |
| Aldimine | amine |
| Ketimine | amine |
| ketene-imine | amine |
| Nitrile | amine |
| Aziridine | amine |
| Nitro | amine |
| Diazo | amine |
| Isocyanide | amine |
| Enamine | amine |
| Lactone | diol |
| Amide | amine + alcohol |
| Aminoboranes | amine-borane |
| Borazine | amine-borane |
| Olefin | alkane |
| Acetylene | alkane |
| Allene | alkane. |

14. The process of claim 10, which is a solvent-free process.

15. The process of claim 6, wherein the process does not require a hydrogen acceptor.

16. The process of claim 6, which is a homogeneous process.

17. The metal complex of claim 1, wherein the phosphine is $PMe_3$ or $PPh_3$.

18. The metal complex of claim 1, wherein M is Ru or Os.

19. A metal complex of Formula III of claim 1, which is:
a) $RuCl_2$ ($PPh_3$) [$(EtSC_2H_4)_2NH$];
b) $RuHCl(PPh_3)$ [$(EtSC_2H_4)_2NH$];
c) $RuHCl(CO)$ [$(EtSC_2H_4)_2NH$];
d) $RuH(OEt)$ ($PPh_3$) [$(EtSC_2H_4)_2NH$].EtOH; or
e) $RuH_2(PPh_3)$ [$(EtSC_2H_4)_2NH$].

20. A metal complex of Formula III of claim 1, which is:
a) $OsCl_2$ ($PPh_3$) [$(EtSC_2H_4)_2NH$];
b) $OsHCl(PPh_3)$ [$(EtSC_2H_4)_2NH$];
c) $OsHCl$ (CO) [$(EtSC_2H_4)_2NH$].

* * * * *